US009522257B2

(12) United States Patent
Webler

(10) Patent No.: US 9,522,257 B2
(45) Date of Patent: Dec. 20, 2016

(54) INTEGRATED CONTROLLED VOLUME INFLATOR DEVICE, COMPONENTS, AND METHODS OF USE

(75) Inventor: William E. Webler, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1165 days.

(21) Appl. No.: 13/436,724

(22) Filed: Mar. 30, 2012

(65) Prior Publication Data

US 2013/0261601 A1 Oct. 3, 2013

(51) Int. Cl.
*A61M 25/10* (2013.01)

(52) U.S. Cl.
CPC .. *A61M 25/10182* (2013.11); *A61M 25/10187* (2013.11)

(58) Field of Classification Search
CPC ............ A61M 25/10182; A61M 25/10187; G01L 7/00
USPC ............ 604/89, 224, 99.01, 194, 227, 236
See application file for complete search history.

(56) References Cited

U.S. PATENT DOCUMENTS

| | | | |
|---|---|---|---|
| 1,838,039 A * | 12/1931 | Montuori | 604/220 |
| 2,627,757 A * | 2/1953 | Austin | 74/565 |
| 4,583,974 A | 4/1986 | Kokernak | |
| 4,739,768 A | 4/1988 | Engleson | |
| 4,990,139 A | 2/1991 | Jang | |
| 5,236,659 A | 8/1993 | Pinchuk et al. | |
| 5,306,248 A * | 4/1994 | Barrington | 604/97.02 |
| 5,348,538 A | 9/1994 | Wang et al. | |
| 5,389,070 A | 2/1995 | Morell | |
| 5,622,665 A | 4/1997 | Wang | |
| 5,634,910 A | 6/1997 | Kanner et al. | |

(Continued)

FOREIGN PATENT DOCUMENTS

| | | |
|---|---|---|
| EP | 0261831 | 3/1988 |
| EP | 0932053 | 7/1999 |

(Continued)

OTHER PUBLICATIONS

Abbott Cardiovascular Systems, Final Office Action dated Aug. 3, 2009 for U.S. Appl. No. 11/313,477.

(Continued)

*Primary Examiner* — Manuel Mendez
(74) *Attorney, Agent, or Firm* — Blakely Sokoloff Taylor & Zafman, LLC; Tom Babbitt

(57) ABSTRACT

A controlled pressure inflation-deflation device inflates a balloon to occlude a blood vessel by moving a large plunger to provide incremental pressure increases within a syringe. A releasable latch moves a second plunger, positioned within a syringe formed by an inner columnar opening in the large plunger, between an occlusion position and a perfusion position. A three-position switch has a release position to allow the large plunger to move freely, an adjust position to provide the incremental pressure increases, and a lock position to lock the location of the plunger. Pressures at which various balloons (e.g., folded balloons) achieve or nearly achieve a substantially circular cross-section may be extrapolated by inflating balloons with pressures equal and/ or greater than the first occlusion pressure. Balloons may be pre-inflated up to or below the first occlusion pressure to achieve a substantially circular cross-section, prior to increasing the balloon to an occlusion pressure.

23 Claims, 13 Drawing Sheets

(56) References Cited

U.S. PATENT DOCUMENTS

| | | | |
|---|---|---|---|
| 5,704,918 A * | 1/1998 | Higashikawa | ................ 604/191 |
| 6,056,721 A | 5/2000 | Schulze | |
| 6,129,737 A | 10/2000 | Hamilton et al. | |
| 6,234,996 B1 | 5/2001 | Bagaoisan et al. | |
| 6,258,080 B1 | 7/2001 | Samson | |
| 6,277,093 B1 | 8/2001 | Lee | |
| 6,368,316 B1 | 4/2002 | Jansen et al. | |
| 6,585,718 B2 | 7/2003 | Hayzelden et al. | |
| 6,641,573 B1 | 11/2003 | Parodi | |
| 7,112,357 B2 | 9/2006 | Miller et al. | |
| 7,169,170 B2 | 1/2007 | Widenhouse | |
| 2001/0001812 A1 | 5/2001 | Valley et al. | |
| 2002/0052638 A1 | 5/2002 | Zadno-Azizi | |
| 2002/0077690 A1 | 6/2002 | Wang | |
| 2003/0094736 A1 | 5/2003 | Qin et al. | |
| 2004/0133156 A1 | 7/2004 | Diaz et al. | |
| 2005/0015048 A1 | 1/2005 | Chiu et al. | |
| 2005/0090802 A1 | 4/2005 | Connors et al. | |
| 2005/0256503 A1 | 11/2005 | Hall | |
| 2005/0256508 A1 | 11/2005 | Hall | |
| 2006/0100511 A1 | 5/2006 | Eriksen | |
| 2006/0149189 A1 | 7/2006 | Diamond et al. | |
| 2007/0010787 A1 | 1/2007 | Hackett et al. | |
| 2008/0114316 A1 | 5/2008 | Christensen et al. | |
| 2010/0191220 A1 | 7/2010 | Webler et al. | |

FOREIGN PATENT DOCUMENTS

| | | |
|---|---|---|
| WO | WO-2004007735 A1 | 1/2004 |
| WO | WO-2004/080508 | 9/2004 |

OTHER PUBLICATIONS

Abbott Cardiovascular Systems, European Examination Report dated Feb. 7, 2011 for EP 06838275.3.

Abbott Cardiovascular Systems, Non-final Office Action mailed Aug. 29, 2011 for U.S. Appl. No. 12/705,556., 13 pages.

Abbot Cardiovascular Systems, Final office action dated May 29, 2012 for U.S. Appl. No. 12/705,556.

Webler, et al., "PCT Search Report and Written Opinion of the International Searching Authority", mailed May 24, 2007; PCT/US2006/045205, filed Nov. 21, 2006.

Webler, et al., "International Preliminary Report on Patentability", mailed Jun. 24, 2008, PCT/US2006/045205, filed Nov. 21, 2006.

Abbott Cardiovasular Systems, Final Office Action mailed Jun. 9, 2014 for U.S. Appl. No. 13/776,579.

Abbot Cardiovascular Systems, First Action Interview Pilot Program Pre-Interview Response mailed Dec. 9, 2013 for U.S. Appl. No. 13/776,579.

\* cited by examiner

INTEGRATED CONTROLLED VOLUME INFLATOR DEVICE, COMPONENTS, AND METHODS OF USE

FIELD

Temporary blood vessel occlusion devices and methods.

BACKGROUND

It is increasingly important that a physician or surgeon delivering substances, such as an imaging or treatment agent or drug, is able to safely, efficiently and accurately occlude a blood vessel at a region of interest to visualize or treat a desired target tissue for effective delivery of the substance. Moreover, it is also important that the physician or surgeon is able to efficiently and accurately remove the occlusion of the blood vessel (allow perfusion of the target tissue) after the desired time interval to avoid damage to the desired target tissue, such as by lack of oxygen (ischemia). This is particularly true when the desired volume, concentration and/or resident time of the substance required at the target site cannot be safely and/or effectively achieved by introduction of the substance to a location remote from the target site. Moreover, the physician may only want to treat the diseased portion of an organ or tissue to avoid treating any healthy portion. In a similar manner, a physician or surgeon may use vessel occlusion to selectively deliver an imaging agent or transparent flushing fluid to the inner diameter (ID) of a vessel. For example, an imaging agent may be injected with vessel occlusion or partial occlusion to more easily/selectively visualize the vessel "roadmap", to more easily visualize/measure the tissues that may be subsequently treated, to label a map of such tissues or to observe/measure the tissues' perfusion and/or clearance/wash out characteristics. A transparent flushing fluid may be injected with vessel occlusion, for example, to improve optical coherence tomography (OCT) imaging or the light application of a photodynamic therapy.

For example, to achieve localized treatment of tissue, such as tissue in a heart, physicians and surgeons can use catheters with occlusion devices, such as balloons. Specifically, blood vessels, such as arteries and veins, can be temporarily occluded during treatment by inflating a balloon at a region of interest of the vessel to block blood flow and thus avoid or retard the washing away of the imaging or treatment agent or drug by the flowing blood. After treatment, the region of interest may then be perfused (blood allowed to flow through the region) by deflating the balloon to unblock the vessel.

In some embodiments, cardiovascular guide catheters are generally percutaneous devices used to advance through a vasculature of a patient proximal to a region of interest and are devices through which another catheter or device may be inserted. Similarly, guidewires may be advanced through a guide catheter and further into the vasculature, across a vascular region of interest. Infusion or delivery catheters are generally catheters used to deliver or infuse a treatment and/or imaging agent to a region of interest in a vasculature of a patient and typically may be engaged with a guidewire and inserted through another catheter (e.g., a guide catheter) and advanced into the vasculature to the desired region of interest. Moreover, occlusion devices, such as occlusion balloons, may be attached to a guide catheter, a guidewire or an infusion catheter to occlude and then perfuse (remove the occlusion and allow blood flow through) a region of interest in a vasculature. Additionally, a guide catheter or infusion catheter may be used to deliver or infuse a treatment and/or an imaging agent to a region of interest in a vasculature of a patient proximal or distal to the occlusion device before, during or after an occlusion.

In addition, an inflation-deflation device may push fluid into and retract fluid from the interior or cavity of the occlusion device or balloon via a catheter to inflate and deflate the occlusion device or balloon (e.g., such as using a lumen or tube in the catheter to communicate a fluid between the inflation device and the inner chamber of a balloon). To help control the outer diameter of a balloon and for safety reasons, the catheter and balloon may be aspirated (remove air and replace it with a fluid) prior to inflating the balloon with fluid to occlude the blood vessel. The fluid most often used to aspirate the catheter and balloon and inflate the occlusion balloon is contrast or a mixture of contrast and saline. Contrast is an imaging agent that allows the balloon to be imaged by an imaging modality such as fluoroscopy, MRI or ultrasound. Occlusion of the vessel is generally confirmed by injecting contrast into the guide catheter and observing by fluoroscopy that none of this contrast flows past the inflated balloon and/or by observing a pressure change due to the occlusion (i.e. the pressure of the blood may be monitored via a lumen of the catheter). Balloons may be made of a variety of materials and their inflation controlled to create non-compliant, compliant and elastic balloons. A non-compliant balloon, like those commonly used on balloon dilation catheters, may be used at moderate or low pressures (compared to dilation pressures) to occlude a vessel safely over a very small range of vessel diameters. However, conventional means to determine a vessel's inner diameter (usually fluoroscopy) are not highly accurate, especially in eccentric vessels/vessels with atheroma. If the device balloon size chosen is too small, then adequate vessel occlusion may not be obtained. If the device balloon size chosen is too large, then the vessel wall may be unnecessarily damaged by over expansion in a manner that may result in a dissection and/or a subsequent vessel stenosis or restenosis. Generally, a compliant, small volume balloon may be used to allow for more rapid balloon inflations and deflations and for more adjustable balloon diameters to allow vessel occlusion over a wider range of vessel diameters at lower balloon pressures. Generally, an elastic, small volume balloon allows for far more adjustable balloon diameters to allow vessel occlusion over a much wider range of vessel diameters at even lower balloon pressures. The difference between a compliant balloon and an elastic balloon is that a compliant balloon will not return to very nearly its original uninflated size (OD) or shape after inflation to its maximum designed size (OD), whereas an elastic balloon will return to its original uninflated size (OD) and shape after inflation to its maximum designed size. Often a compliant balloon will have an initial, pre-insertion, or nominal ID that is larger than the outer diameter (OD) of the catheter/device that it is mounted on and, thus, the compliant balloon will be folded to hug the catheter/device shaft during insertion into a vessel. Often the ID of an elastic balloon will closely fit to the OD of the catheter/device that it is mounted on and not require folding. Lower inflation pressures are desired, as less pressure is then available to damage/expand the vessel wall, if the balloon is over-sized due to an accidental misadjustment, an incorrect vessel size determination or other reasons. As a lower limit, the inflation pressure applied to or present inside an occlusion balloon must exceed the blood pressure of the vessel to keep the balloon inflated and occluding that vessel. Small volume balloons are desired because of their more rapid inflation and deflation times at low pressures. A wide range of balloon diameter adjustment is desired, as fewer devices may be stocked to cover a particular vessel size range (vessel sizes vary in the anatomy and across the population) and the degree of vessel diameter determination accuracy required to choose a device that will safely occlude the vessel is reduced. In some embodiments, what is desired is inflation/deflation, aspiration, and occlusion balloon devices and procedures that allow for repeated occlusion and perfusion of a blood vessel with a low risk of damaging/significantly expanding the vessel wall. For instance, there is a need for an occlusion balloon, such as a compliant small volume low pressure balloon, that will expand with predictable repeatable outer diameter increments in response to being inflated and deflated with predictable repeatable amounts of fluid or pressure increments that can be provided by an inflation/deflation device (after successful aspiration).

SUMMARY

There is disclosed an inflation-deflation device for inflating and deflating an occlusion device or a balloon using increments of selected, controlled, or equal changes in pressure and/or volume of a fluid. A preferred embodiment of such an inflation-deflation device, without limitation to any single or combinations of components or functions thereof, may be a controlled change in pressure and/or volume inflation deflation device, such as an "INDEFLATOR®" which is a trademark of Guidant Corporation, 3200 Lakeside Drive, Santa Clara, Calif. 95054-2807. The inflation-deflation device may include functionality to inflate (and deflate) an occlusion device or balloon using increments of selected, controlled, or equal changes in pressure of fluid, such as to initially occlude a vessel. Subsequently, such an inflation-deflation device may also include a different functionality to deflate or remove a volume of fluid from the balloon sufficient to allow perfusion of the blood vessel, and then re-inflate or increase the volume of fluid in the balloon by the same amount as removed, to re-occlude the blood vessel. This may be done independently of the changes in pressure or volume used to initially occlude the vessel. An inflation deflation device with only this different functionality may be referred to as a controlled volume INDEFLATOR® (or CVI). An inflation-deflation device with the functionality to initially occlude a vessel and the different functionality to repeatedly deflate and re-inflate the balloon to remove and then re-apply the initial vessel occlusion may be referred to an integrated controlled volume INDEFLATOR® (or ICVI). The device of the present invention is an ICVI and can be especially useful when used with compliant or elastic balloons. The inflation-deflation device may have a syringe, which consists of a body and a plunger, to push in and retract out fluid communicated with the interior or cavity of the balloon via a catheter or lumen therethrough.

In some embodiments, a single plunger may be controlled by one mechanism to provide the increments of pressure or volume for the initial occlusion, and another mechanism to deflate and re-inflate with the controlled volume for subsequent perfusion and occlusion. Alternatively, a plunger within a plunger design may be used. In such embodiments, a large plunger may be moved to provide the incremental changes in pressure or volume for initial occlusion, while a smaller plunger within the shaft and larger plunger may be used to remove and re-inflate with the controlled volume for subsequent perfusion and occlusion.

The device may also have a releasable latch between a proximal portion, which constrains the syringe's plunger via a longitudinal incremental manipulation mechanism, and a distal portion, which constrains the body of the syringe, so that releasing the latch allows for relative motion between the proximal housing and the distal housing. Thus, the plunger may be moved a distance into or out of the body of the syringe. Specifically the latch may define two releasably latched positions to move the plunger a set distance within the syringe body.

Prior to using increments of pressure or volume to inflate the balloon to initially occlude the vessel, when the described inflation-deflation device is used to control the diameter of balloons that have an initial or nominal diameter or a desired initial diameter or inflation that requires an initial pressure or volume of fluid to be injected into the balloon (via a catheter, a communicating lumen and/or cavity), the balloon may also be initially inflated by the pressure or volume using the same device. For instance, a compliant balloon may be initially inflated to an initial pressure or initial volume using the inflation-deflation device to inflate the balloon to a low pressure or a low volume, and then the balloon may be further inflated using increments of pressure or volume until the blood vessel is occluded using the same inflation-deflation device. These device designs may include a low pressure Indeflator® that also has the different function of portions can be moved apart to deflate the balloon and then moved back together to the original position to re-inflate the balloon back to its original/initial inflation conditions (same volume of fluid in the catheter/balloon) to attain the same vessel occlusion.

Some embodiments will include a switch with a lock position to ensure that the plunger (e.g. single or large plunger) can be locked in position preventing its accidental rotation/position change or being moved by a "back pressure" of fluid in the syringe (e.g. from the balloon). Embodiments also include the switch having a release position to allow the plunger to move in response to such back pressure or in response to a user pushing or pulling a knob attached to a shaft of the plunger. Embodiments also include the switch having an adjust position that prohibits the plunger from moving in response to a back pressure, but allows the plunger to be moved via a threaded mechanism when the user rotates the knob, but prohibits user from pushing or pulling the knob to move the plunger. In some embodiments, the adjust and lock positions are adjacent so that the switch can be moved between the adjust and locked positions without encountering the release position.

Some of the indeflators will incorporate a pressure gauge as a component or have a pressure gauge coupled to them to measure the pressure in the system. A mechanical pressure gauge generally has a design that often traps a significant amount of air relative to electronic type pressure gauges. All embodiments consider aspirating the balloon inflation/deflation system, by removing air and replacing the air with fluid, to minimize the system (e.g. the Indeflator®, balloon catheter, and optionally balloon) compliance (change in volume per unit change in pressure) thus limiting compliant balloon outer diameter (OD) creep. However, in balloon inflation/deflation systems with a mechanical pressure gauge, extra care and attention must be exercised to remove the air from the mechanical pressure gauge.

In a low compliance system, when the balloon OD is set at given pressure, such that the balloon is inflated above its nominal OD, a compliant balloon material creeps (slowly elongates/stretches over time) and thus, the volume of the balloon/system increases and the pressure drops rapidly, reducing the forces causing the creep and limiting the rate and extent creep and, thus limiting the balloon OD creep. In a pressure incremented (balloon OD incremented) system, some embodiments include small/smaller pressure increments in the pressure range up to the pressure at which the balloon material will be firmly pressed up against the vessel wall (usually 1 ATM pressure and below) in the case where the balloon's nominal OD is greater than the vessel's ID.

Embodiments also include extrapolating balloon test pressures and OD's to determine a nominal pressure or first occlusion pressure, such as for low pressure compliant balloons that include pre-inflation folds or wrinkles.

BRIEF DESCRIPTION OF THE DRAWINGS

Various features, aspects and advantages will become more thoroughly apparent from the following detailed description, the set of claims, and accompanying drawings in which:

DETAILED DESCRIPTION

Disclosed are inflation-deflation devices for inflating and deflating an occlusion device or a balloon using increments of selected, controlled, or equal changes in pressure and/or volume of a fluid. The inflation-deflation device may inflate (and deflate) an occlusion device or balloon using increments of selected and controlled, equal changes in pressure of fluid, such as to initially occlude a vessel. Subsequently, such an inflation-deflation device may also remove a sufficient volume of fluid from the balloon to allow perfusion of the blood vessel, and then re-infuse the removed volume of fluid into the balloon to re-occlude the blood vessel. This may be done independently of the changes in pressure or volume used to initially occlude the vessel. Thus, such an inflation deflation device may also be referred to as an integrated controlled volume INDEFLATOR® (or ICVI). The inflation-deflation can be especially useful when used with noncompliant, compliant or elastic balloons used for vessel occlusion. The inflation-deflation device may have a syringe, which consists of a body and a plunger, to push in and retract out fluid communicated with the interior or cavity of the balloon via a catheter or lumen therethrough.

Figure 1A:
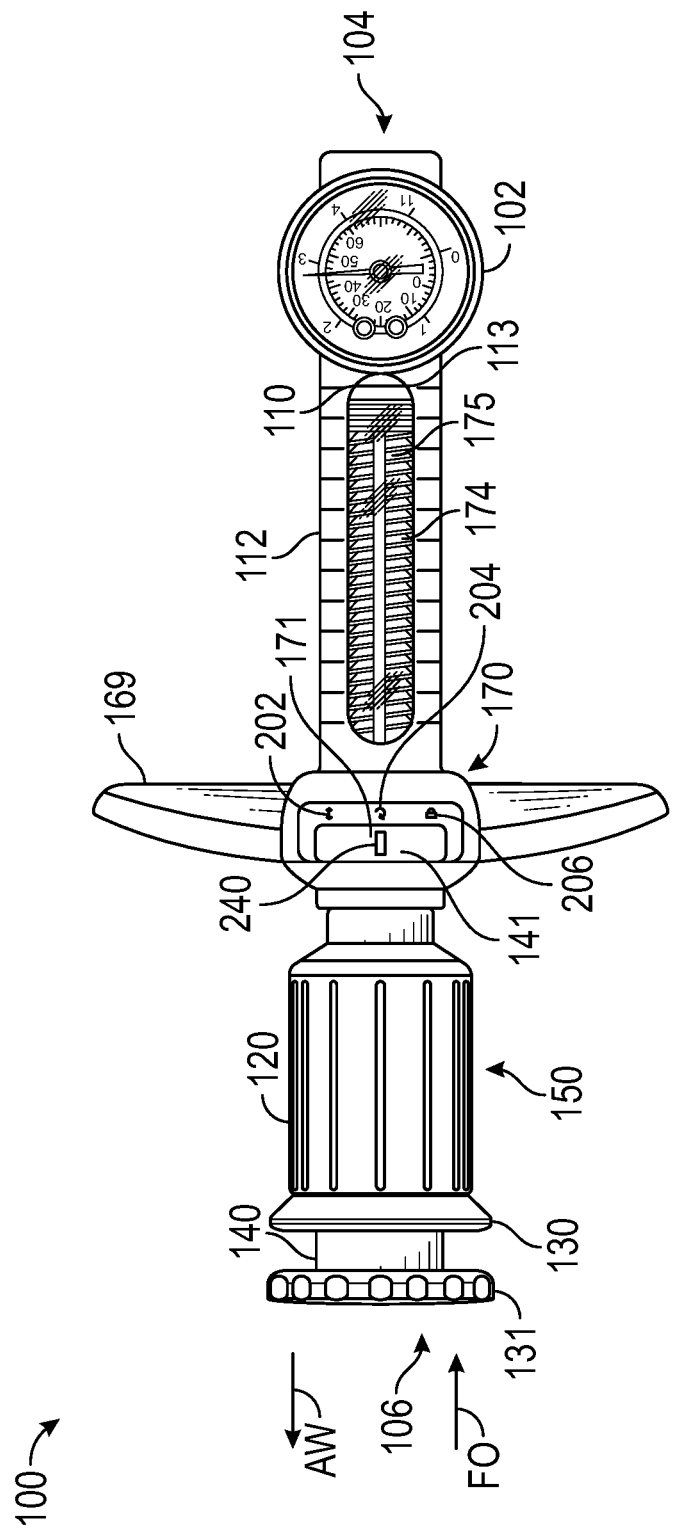
FIGS. 1A-1H are schematic views of various components of a first embodiment of an inflation deflation device.

FIGS. 1A-1H are a schematic perspective view of various components of a first embodiment of an inflation deflation device. FIG. 1A. FIG. 1A shows inflation deflation device 100 having proximal end 106 and distal end 104. Device 100 has knob 131 attached to proximal housing 140 and rotational knob 130 attached to distal housing 120. Proximal housing 140 is positioned relative (e.g. attached or coupled) to distal housing 120 by releasable latch 150. Distal housing 120 is attached to syringe barrel 112 having plunger seal 110 (which may be referred to as a "plunger" herein) disposed there within and having syringe tip 113. Plunger seal 110 is coupled by shaft 174 to screw mechanism 170 and three position switch 171. Screw mechanism 170, switch 171, and syringe barrel 112 are housed within T handle 169. T handle 169 is shown having window 175 through which shaft 174, syringe barrel 112 and plunger seal 110 are visible. However, window 175 is optional and excluded from certain embodiments. Gauge 102 is shown mounted on T handle 169 and is in fluid communication with the inside of syringe barrel 112. Proximal housing 140 is coupled to a shaft and plunger within shaft 174 and in fluid communication with the inside of syringe barrel 112.

Figure 1B:
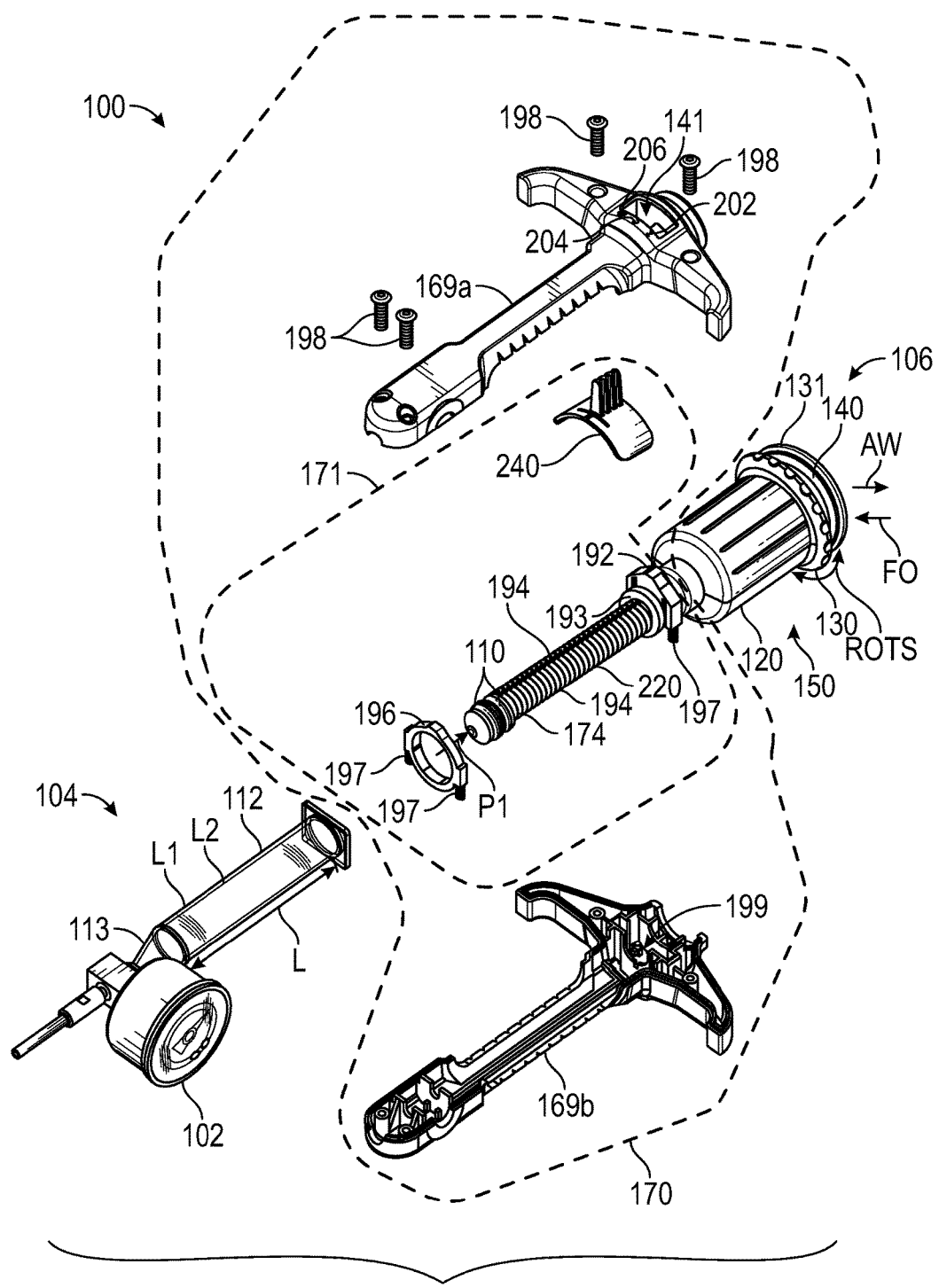

FIG. 1B shows syringe barrel 112 having length L, and location L1 and L2. FIG. 1B also shows T handle 169 including T handle halves 169a and 169b attachable by fasteners 198. Can be appreciated that T handle 169 may include more or fewer pieces than two halves. Also note that various components described herein may be made of various materials including polymer, rubber, plastic, metal, wood, organic materials, inorganic materials, synthetic materials, molded materials, galvanized materials, stainless materials, injected materials, forged materials, ceramic materials, glass, resin, epoxy, and the like.

FIG. 1B shows switch 171 including lever 240, lock 192, lock ring 193, shaft 174, slots 194, and gear 196 (which may all be mounted within mount 199 of T handle 169). The components of switch 171 may be included in screw mechanism 170. In some embodiments, screw mechanism 170 includes T handle 169 but excludes lock ring 193, gear 196, and lever 240. Gear 196 and lock 192 may each be mounted on springs 197 and 297 within mount 199.

Screw mechanism 170 may also include distal housing 120 and rotational knob 130, such than when knob 130 is rotated in direction ROTS the screw mechanism moves plunger seal 110 along length L within syringe barrel 112. For example, plunger seal 110 may move distally when in knob 130 is rotated in a clockwise direction relative to the proximal end, and plunger seal 110 moves proximally when knob 130 is rotated counter-clockwise direction relative to the proximal end. In some embodiments, screw mechanism 170 includes a plurality of incremental positions to locate plunger seal 110 at along length L of the syringe that cause incremental and equal increases or decreases in fluid volume output by syringe barrel 112 when the syringe is filled with fluid and the plunger is transitioned between the positions.

Switch 171 may also include window 141, such as having lever 240 extending through window 141 and movable, by a user, between three positions within the window. Moving the lever may cause switch 171 to be moved between three positions (e.g., from one position to an adjacent position) by a user (e.g., a surgeon). Switch 171 may have a lock position to ensure that the plunger (e.g. large plunger seal 110) can be locked at a position without rotation or being moved by a "back pressure" of fluid in the syringe (e.g. from an occlusion balloon). Switch 171 may have a release position to allow plunger seal 110 to move in response to such back pressure or in response to a user pushing or pulling a knob attached to a shaft of the plunger. Switch 171 may also have an adjust position that prohibits the plunger from moving in response to a back pressure, but allows the plunger to be moved in increments of motion when user rotates knob 130/distal housing 120, but prohibits user from pushing or pulling knob 130/distal housing 120 to move the plunger seal 110. In some embodiments, the adjust and lock positions are adjacent so that the switch can be moved between the adjust and locked positions without encountering the release position.

Figure 1C:
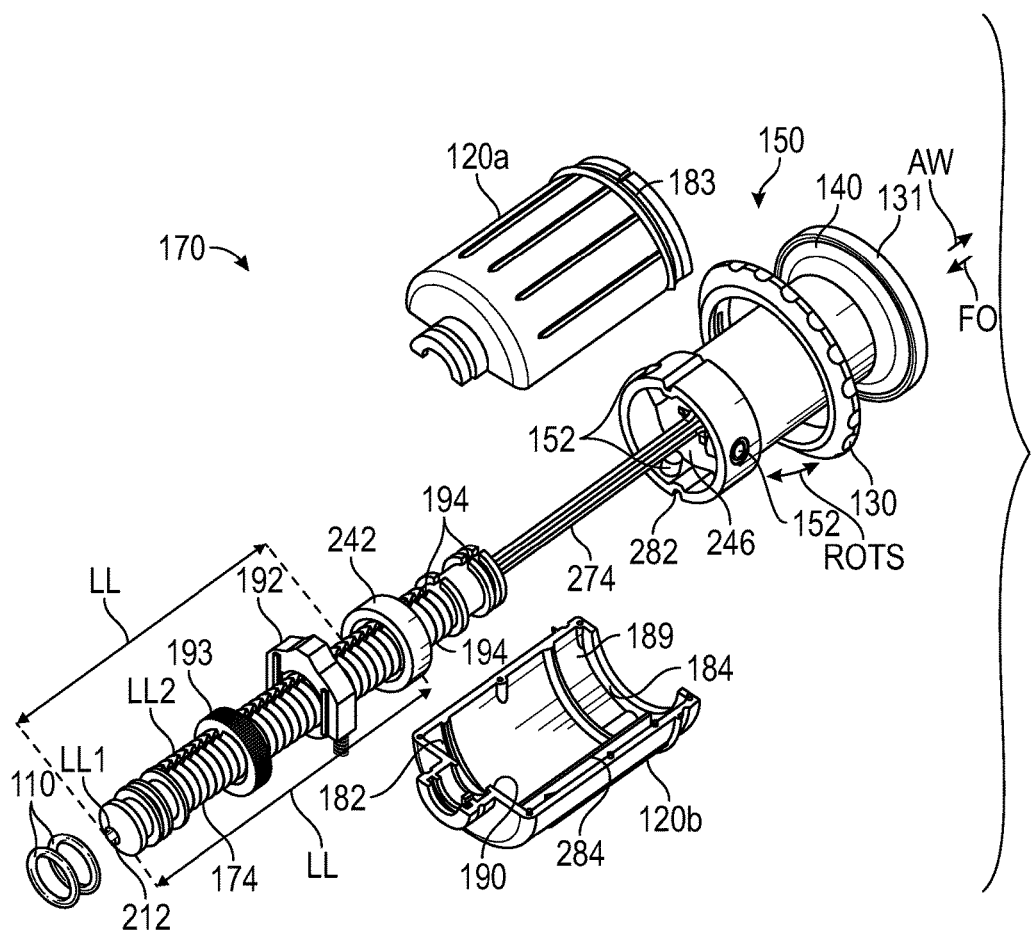

FIG. 1C shows some components of screw mechanism 170 and the components of latch 150. FIG. 1C shows distal housing 120 having halves 120a and 120b. However, as noted above for T handle 169, distal housing 120 may be more or fewer pieces than two halves. FIG. 1C also shows releasable indexing locks 152 (for example, a device or construction often called a ball nosed spring plunger or the like) on an outer perimeter of proximal housing 140, such as for engaging internal recesses of distal housing 120. Thus, movement of the housing 140 away AW and towards FO housing 120 may be releasably constrained by locks 152 engaging recesses 182 and 184. Movement of the housing in direction AW may also be mechanically restrained by stop 189 engaging surface of proximal housing 140. Movement of the housings towards each other FO may be mechanically restrained or stopped by the distal end of proximal housing 140 engaging or coming into contact with stop 190. Knob 130 may be mounted in or attached to and retained by recess 183 of distal housing 120. Knob 130 holds together the proximal portions of distal housing portions 120a and 120b in a manner such that, when assembled, knob 130 and distal housing 120 are rotationally and longitudinally locked relative to each other.

Screw mechanism 170 may include slots 194 in threads 220 of shaft 174, as shown. Although two slots are shown it can be appreciated that in some embodiment 1, 3, 4, or another number of slots may be used. Screw mechanism 170 is also shown including holder 242 for holding together the distal portions of distal housing portions 120a and 120b in a manner such that they are locked together over the proximal portion of shaft 174, securing it within the distal housing and engaging slots 194 such that shaft 174 is also rotationally locked relative to the distal housing. The proximal portions of distal housing portions 120a and 120b are held together by the attachment of knob 130. Base 246 (See FIG. 1D for more detail) couples proximal housing 140 to internal shaft 274, which resides or is disposed within second syringe barrel 212 inside of shaft 174. FIG. 1C shows plunger seal 110 comprising two o-rings to be mounted on shaft 174, it can be appreciated that various other seal designs, such as a single tubular seal component or a single o-ring may be used for plunger seal 110 to form a seal against the ID syringe barrel 112.

Plunger seal 210 (which may be referred to as a "plunger" herein) may have an o-ring, o-rings or other seal configuration mounted on its distal end, which interacts with the ID of the shaft 174 (second syringe barrel 212) to form a second syringe. The ID configuration of the shaft 174 (second syringe barrel 212) interacts with the OD configuration of the internal plunger seal 210 to form a liquid seal and communicates with the ID of syringe barrel 112 so that movement of plunger seal 210 (e.g., smaller or internal plunger or plunger seal 210, as compared to larger plunger seal 110) also reduces or increases the volume within syringe barrel 112 and any other system volumes that inflation deflation device 100 is placed into fluid communication with.

According to embodiments, internal shaft 274 may not rotate with respect to second syringe barrel 212 and shaft 174. For example, recesses 282 of proximal housing 140 may engage ridge 284 of distal housing 120 to prevent rotation of the proximal housing 140 (e.g., and internal shaft 274) with respect to the distal housing 120 (e.g., and second syringe barrel 212). Note that both proximal housing 140 and distal housing 120 are rotationally locked together and may rotate with respect to handle 169, thus allowing rotation of knob 130 (and proximal housing 140 and distal housing 120) to cause screw mechanism 170 to move shaft 174 (and 274) and plunger seal 110 (and 210) along length L (and LL) as will be described in greater detail later.

In some embodiments, the location along length L of plunger seal 110 along syringe barrel 112 may be controlled by screw mechanism 170 to provide the increments of fluid volume or to adjust the pressure within an occlusion balloon (e.g., within syringe barrel 112) for initial occlusion. In some cases, after occlusion, another mechanism (not shown) may be used to deflate and re-inflate the occlusion balloon with the controlled volume for subsequent perfusion and occlusion, by also controlling the location of plunger seal 110 along length L of syringe barrel 112.

Alternatively, a plunger within a plunger design may be used. For example, after occlusion, syringe barrel 212, plunger seal 210, shaft 274 and knob 131 may be used to deflate and re-inflate the occlusion balloon with the controlled volume for subsequent perfusion and occlusion, by controlling the location of plunger seal 210 along length LL of syringe barrel 212. In such embodiments, large plunger seal 110 may be moved to provide the incremental changes in pressure or volume for the initial occlusion, while smaller plunger seal 210 within the shaft 174 (second syringe barrel 212) and within larger plunger seal 110 may be used to remove fluid from the balloon and then re-inflate the balloon with the controlled volume (the same volume by which it was initially inflated) for subsequent vessel perfusion and occlusion.

For example, releasable latch 150 may include knob 131 that when pulled away (see direction AW) from distal housing 120 puts latch 150 in a perfusion position, and when pushed towards (see direction FO) distal housing 120 puts latch 150 in an occlusion position. Knob 131 may be pulled away and pushed towards the distal housing by a user of device 100 grabbing distal housing 120 with one hand and grabbing knob 131 or proximal housing 140 with the other hand and pulling them away from each other or pushing them towards each other.

Latch 150 may be described as including proximal housing 140, which constrains the plunger seal 210 via a longitudinal incremental manipulation mechanism (e.g., knob 131, proximal housing 140, shaft 274), and distal portion 120, which constrains the body of the syringe barrel 112. Thus, releasing the latch allows for relative motion between the proximal housing and the distal housing. Thus, plunger seal 210 may be moved a distance into or out of syringe barrel 212. Specifically the latch may define two releasably latched positions (occlude and perfuse) to move plunger seal 210 a set distance (e.g., between locations LL1 and LL2) within syringe barrel 212.

Figure 1D:
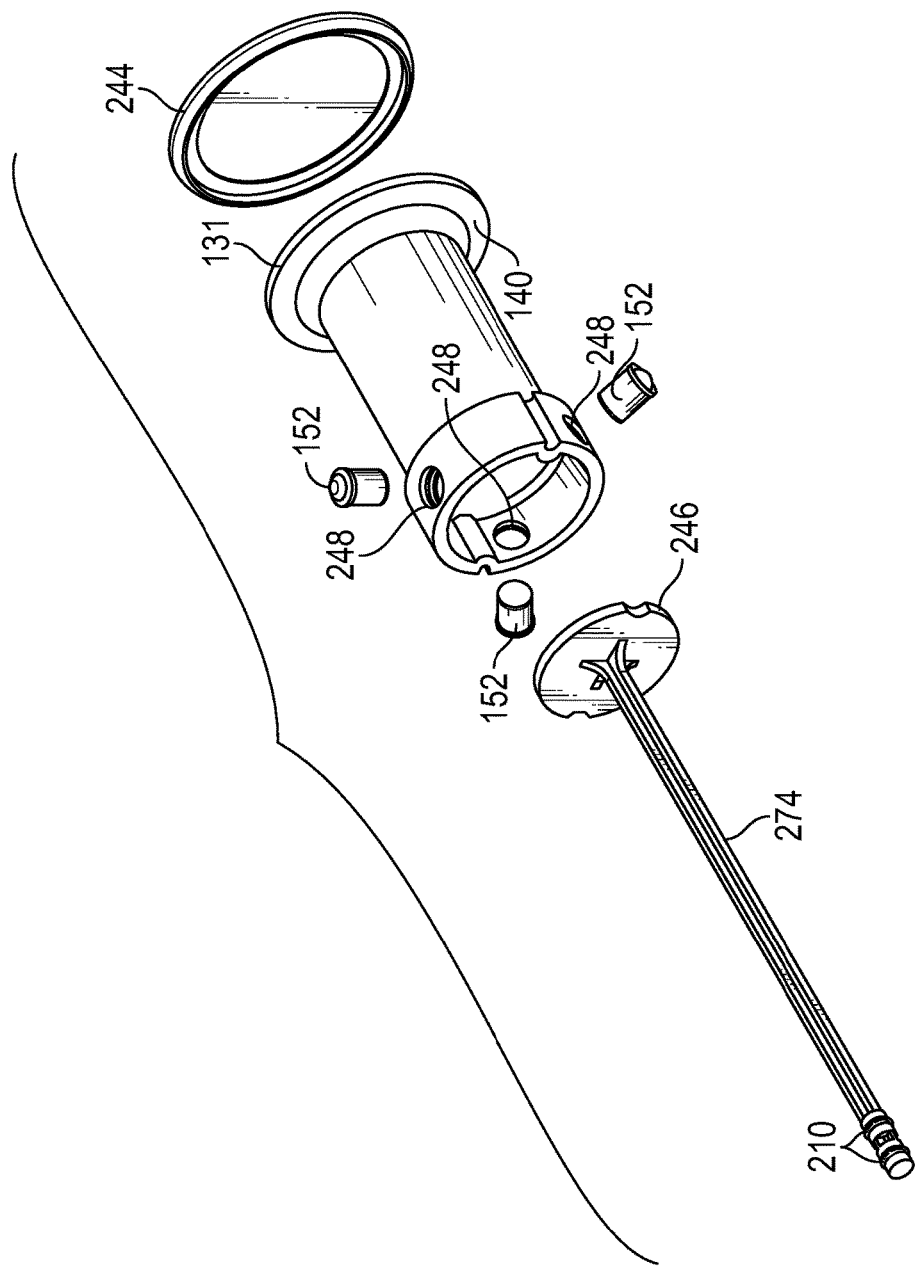

FIG. 1D shows internal shaft 274 having internal plunger seal 210, such as a plunger to form a liquid tight seal within second syringe barrel 212. Thus, plunger seal 210 may be moved along length LL within second syringe barrel 212 which may be a cylindrical shaped opening formed through the inside of shaft 174 (e.g., see FIG. 1C). Internal plunger seal 210 is shown including two o-rings, but may include other designs, as described above for plunger seal 110. Indexing locks 152 are shown disposed within openings 248 in housing 140. Knob 131 is also shown including optional cover 244. In some embodiments, cover 244 incorporates knob 131 and provides a convenient proximal surface to push against when pushing knob 131 relative to rotational knob 130 and/or distal housing 120 to return latch 150 to the occlusion position, as will be described later.

Gauge 102 may be a pressure gauge to measure the pressure in the system (e.g. the Indeflator®, balloon catheter, and optionally balloon), such as the pressure of fluid within syringe barrel 112. Because they are in direct fluid communication, the pressure within syringe barrel 112 will be the same as the pressure within syringe barrel 212. Gauge 102 may be a mechanical pressure gauge that can be aspirated by removing air and replacing the air with fluid, to minimize the system compliance (change in volume per unit change in pressure) thus limiting compliant balloon outer diameter (OD) creep.

According to embodiments, releasable latch 150 positions proximal housing 140 relative to distal housing 120, which is attached to syringe barrel 212. Shaft 174 is hollow (has and ID) forming second syringe barrel 212, within syringe barrel 112. Screw mechanism 170 couples syringe barrel 212 (e.g., ID of shaft 174) and plunger seal 110 to rotating knob 130 to move plunger seal 110 along length LL of syringe barrel 112 when the knob is rotated. Internal shaft 274 attaches plunger seal 210 to knob 131 of proximal housing 140. Thus, when latch 150 positions proximal housing 140 relative to distal housing 120, latch 150 also moves shaft 274 and plunger seal 210 within syringe barrel 212. In some embodiments, latch 150 attaches or couples proximal housing 140 to plunger seal 210 within syringe barrel 212 to releasably lock plunger seal 210 at a first location (e.g., location LL1 of FIG. 1C) along length LL of the syringe barrel 212, and to releasably lock plunger seal 210 at a different second location (e.g., location LL2 of FIG. 1C) along length LL of syringe barrel 212.

More specifically, when knob 131 is moved in direction FO, when locks 152 engage (e.g., are releasably locked) into recesses 182, or when proximal housing 140 is maintained against stop 190, latch 150 may be releasably locked into an occlusion position. The latch may be releasably locked into an occlusion position, such as by causing internal shaft 274 to move or maintain plunger seal 210 at location LL1 along length LL within second syringe barrel 212 (e.g., see FIGS. 1A and 1G); the position of plunger seal 110 within syringe barrel 112 having been previously adjusted to inflate the balloon to occlude the vessel with the latch 150 in this position. Note that syringe barrel 112 is not shown in FIGS. 1A and 1G to be in a balloon inflation position. Barrel 112 is shown in FIG. 1A in a maximum distal position, and is shown in FIG. 1G in maximum proximal position. A balloon inflation position for barrel 112 is typically between the positions shown in FIGS. 1A and 1G. However, when knob 131 is moved in direction AW, when locks 152 engage (e.g., are releasably locked) into recesses 184, or when proximal housing 140 is maintained against stop 189, latch 150 may be releasably locked into a perfusion position. The latch may be releasably locked into a perfusion position, such as by causing internal shaft 274 to move or maintain plunger seal 210 at location LL2 along length LL within second syringe barrel 212 (e.g., see FIGS. 1C and 1H); the change in syringe volume between positions LL1 and LL2 being designed to be sufficient to deflate the balloon For example, FIG. 1H may show shaft 274 moved proximally (e.g., from the distal position shown in FIG. 1G), such as by pulling knob 131 in direction AW to put latch 150 in perfusion position (e.g., from occlusion position of FIG. 1G), while switch 171 is in the locked position 206. In some cases, latch 150 should not be moved from its occlusion position, unless the switch is in the locked position. In the adjust position, the fluid back pressure on the plunger and transmitted to the threaded portion of screw mechanism 170 can cause the handle to rotate and a manner that tends to deflate the balloon when the latch 150 position is changed. This means that you can lose your initial occlusion inflation setting, which can cause a treatment to fail. It can be appreciated that after FIG. 1H, FIG. 1G may show shaft 274 moved distally (e.g., from the proximal position shown in FIG. 1H), such a by pushing knob 131 in direction FO to put latch 150 in occlusion position (e.g., to occlusion position of FIG. 1G), while switch 171 is in the locked position 206.

In some embodiments, plunger seal 110 and screw mechanism 170 are configured to increase a pressure of fluid in syringe barrel 112 to a pressure to cause a balloon to occlude a human blood vessel, and plunger seal 210 and releasable latch 150 are configured to translate seal 210 from an occlusion position, which is the second latched position, to a first latched position to cause perfusion (e.g., by pulling knob 131) and then to the second latched position, the occlusion position to cause re-occlusion of the blood vessel (e.g., by pushing knob 131 relative to rotational knob 130 and/or distal housing 120). It is considered that latch 150 may be repeatedly transitioned between a first latched position to cause perfusion and a second latched position to cause re-occlusion of the blood vessel (e.g., by pulling knob 131, and then pushing knob 131 relative to rotational knob 130 and/or distal housing 120).

In some other embodiments, plunger seal 110 and screw mechanism 170 are configured to incrementally decrease the volume inside syringe barrel 112 to inject increments of fluid volume into a balloon to occlude a human blood vessel, and plunger seal 210 and releasable latch 150 are configured to translate seal 210 from an occlusion position, which is the second latched position, to a first latched position to cause perfusion (e.g., by pulling knob 131) and then to a second latched position, the occlusion position to cause re-occlusion of the blood vessel (e.g., by pushing knob 131 relative to rotational knob 130 and/or distal housing 120). It is considered that latch 150 may be repeatedly transitioned between a first latched position to cause perfusion and a second latched position to cause re-occlusion of the blood vessel (e.g., by pulling knob 131, and then pushing knob 131 relative to rotational knob 130 and/or distal housing 120).

In some embodiments, when latch 150 is in the occlusion latched position, proximal housing 140 is held against a stop surface and/or by locks 152 are held within a recess with enough force to resist at least a 6 ATM inflation pressure without significant longitudinal motion between the proximal and distal housings. When moving to the occlusion latched position from the perfusion latched position, as described above, fluid may be forced into the balloon via a long narrow lumen in the catheter body (a balloon inflation lumen). In practice this is done by rapidly pushing knob 131 relative to the distal housing 120 into the second releasably latched position. However, the long narrow balloon inflation lumen of the catheter presents a significant flow resistance and thus, the pressure in syringe barrels 112 and 212, pressure gauge 102 and any other fluid communicating components proximal of the catheter will rise rapidly and then decline as fluid flows down the balloon inflation lumen to re-inflate the balloon to its occlusion diameter (or condition). If the occlusion position retaining force of latch 150 was only set to slightly above the force required to retain the occlusion position against the pressure required to hold the balloon inflated to re-attain the occlusion and resist accidental/incidental applied forces, then latch 150 would be unable to retain the occlusion position until the balloon was nearly fully re-inflated (fluid flow down the balloon inflation lumen was significantly reduced). Thus, the operator would be required to hold the latch 150 in the occlusion position until the balloon was nearly fully re-inflated. Due to the compliance of practical inflation deflation devices 100, the time to nearly fully re-inflate the balloon can be several seconds or more. It can annoy the operator and/or cause dysfunction of the device 100, if the operator is required to manually hold latch 150 in the occlusion position for several seconds or, if the operator were to let go of the latch 150/set aside device 100 prematurely, the latch were to spontaneously released itself from the occlusion latched position to some other position (usually between the occlusion and perfusion positions). Experimentation with a practical device 100 using a mechanical low pressure gauge 102, coronary sized catheters, small volume compliant occlusion balloons and practical connection tubing indicates that a latch 150 that is designed to be capable of resisting 6 ATM of fluid pressure in the occlusion latched position will remain reliably latched during use. Other device 100, catheter, balloon and/or connection tubing designs may require latch 150 to resist a greater or lesser fluid pressure to reliably remain in the occlusion latched position immediately after being moved from perfusion latched position to the occlusion latched position by the operator.

Also, in some embodiments, when latch 150 is in the perfusion latched position, proximal housing 140 is held against a stop surface and/or by locks 152 are held within a recess with enough force to resist a vacuum in the syringe barrels and/or accidental/incidental applied forces without becoming disengaged from the detent position and the internal plunger seal 210 and shaft 174 are at or near their greatest allowed longitudinal disengagement (balloon deflation position). This design may prevent annoying the operator and/or causing dysfunction of the device 100, when latch 150 is moved from the occlusion latched position to the perfusion latched position in a manner similar to that described above for the move from the perfusion latched position to the occlusion latched position. One main difference being that in the move from the occlusion latched position to the perfusion latched position, the pressure of the fluid in the syringe barrel 112 (and the fluid communicating with it) can not go lower than zero (a vacuum). Thus, if latch 150 resists the forces by generated by 1.5 ATM in the opposite direction (1 ATM to resist the vacuum relative to atmospheric pressure and another 0.5 ATM to resist accidental forces), the latch 150 will remain in the perfusion (balloon deflation) position when moved from the occlusion to the perfusion position.

Figure 1E:
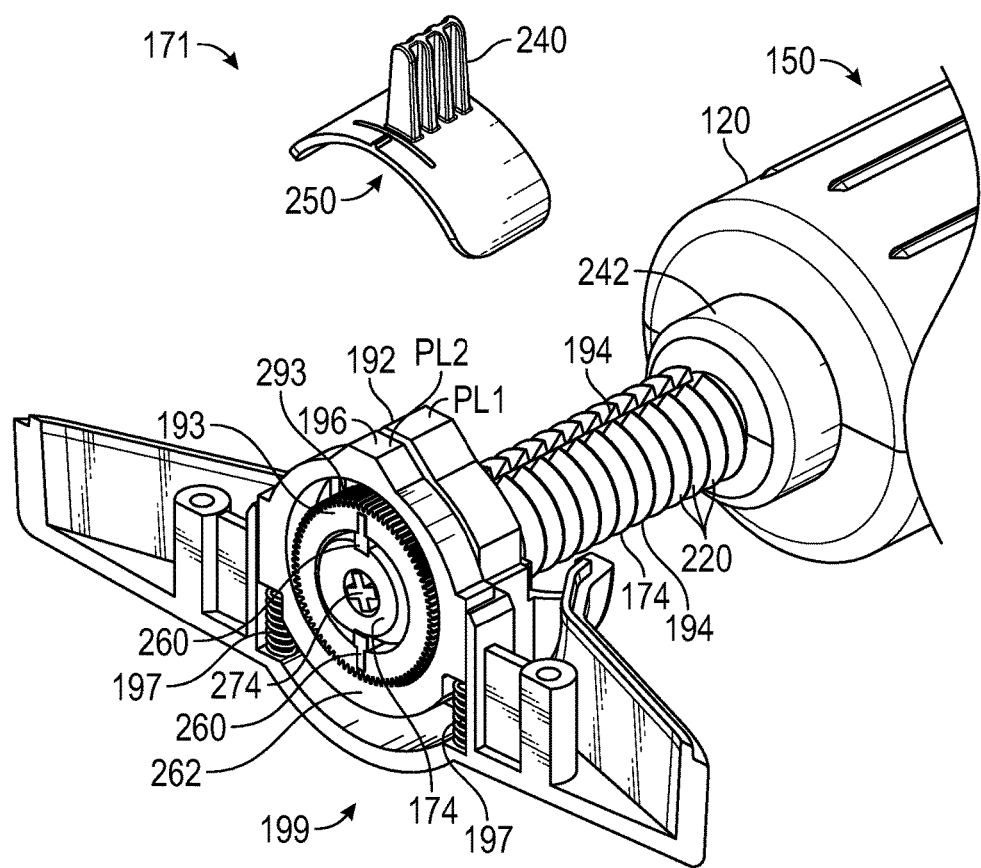
Figure 1F:
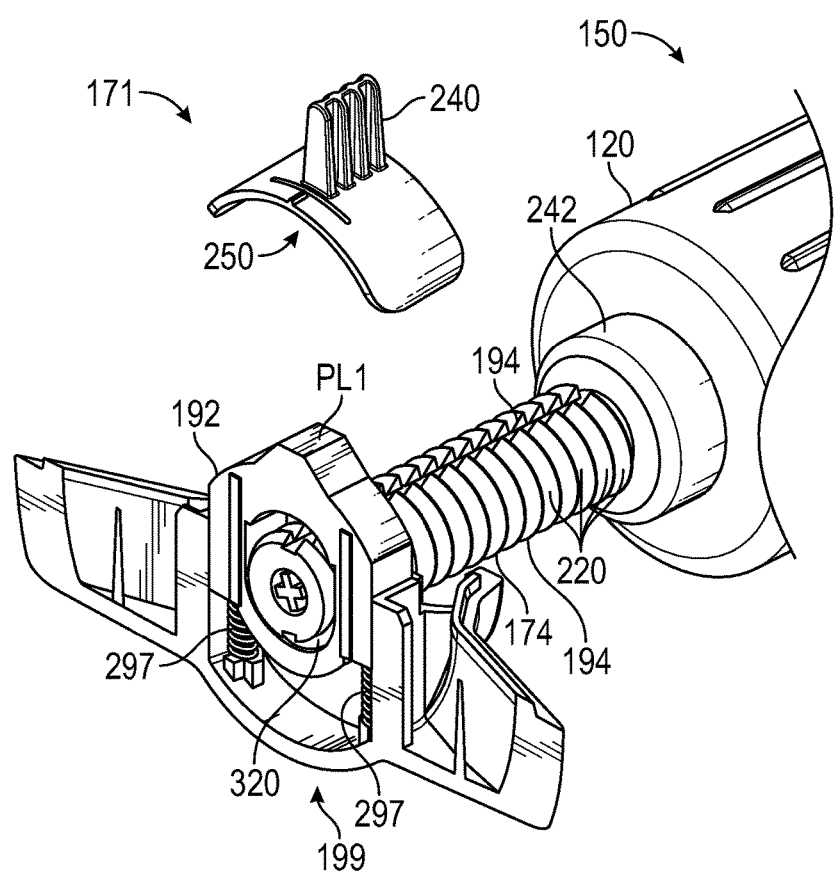
Figure 1G:
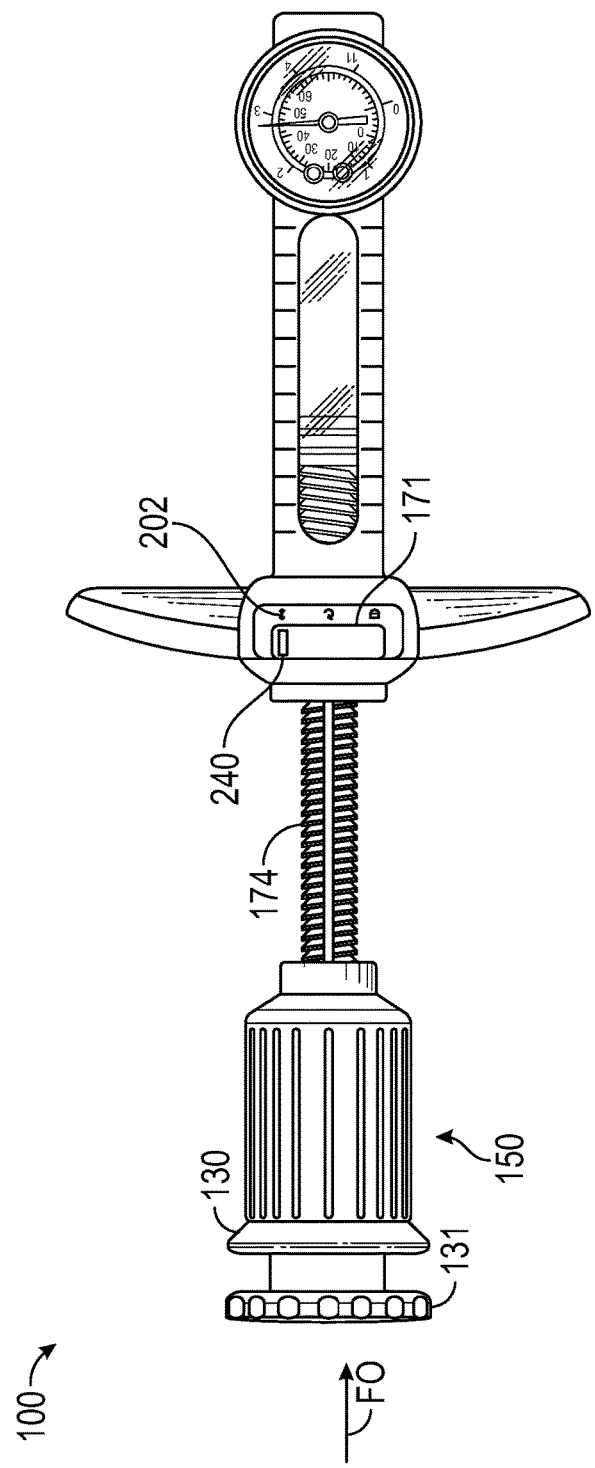
Figure 1H:
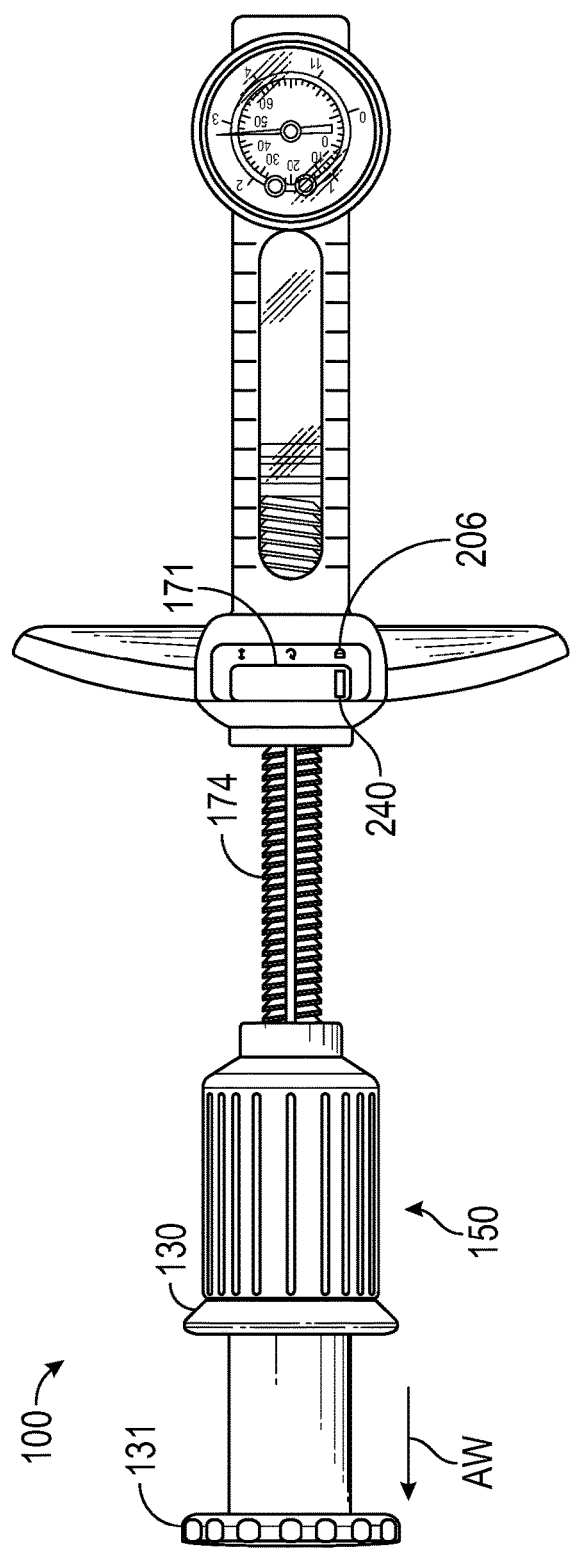

FIGS. 1E and 1F show switch 171 including lever 240, lock 192, lock ring 193, shaft 174 and gear 196 (which may all be mounted within mount 199 of T handle 169). The components of switch 171 may be included in screw mechanism 170. Lock 192 has platform PL1 for engaging bottom 250 of lever 240; and has threads 320 at the bottom inner surface of lock 192 for engaging threads 220. Threads 320 may be a threaded surface for engaging threads 220 (e.g., like a nut engages threads of a bolt) so that when threads 220 rotate, they thread through lock 192, moving shaft 174 distally or proximally, such as noted herein when knob 130 or housing 120 is rotated. Lock 192 is biased by springs 297 away from mount 199, onto which the springs are mounted. Gear 196 has platform PL2 for engaging bottom 250 of lever 240. Gear 196 is biased by springs 197 away from mount 199, onto which the springs are mounted. Gear 196 has catch 262 to engage gears 293. Lock ring 193 has gears 293 for engaging catch 262 located at the bottom inner surface of gear 196; and has engagements 260 for engaging slots 194 of shaft 174. Shaft 174 has slots 194 and threads 220. Catch 262 may engage or lock gears 293 (e.g., the gears of catch 262 lock gears 193 into one rotational position), prohibiting shaft 174 from rotating (e.g., due to engagements 260 of lock ring 293 being locked into slots 194 of the shaft). During this time, if threads 320 are engaging threads 220, then shaft 174 is also prohibited from moving distally or proximally (e.g., shaft 174 can not be moved by rotating knob 130, or otherwise). Bottom 250 may have protrusions and recesses (e.g., a contoured shape) for engaging (e.g., pressing and releasing) platforms PL1 and PL2.

For example, when lever 240 is moved into release position 202, bottom 250 may have protrusions (or other configurations) that press on platform PL1 and PL2 with sufficient force/displacement to cause them to move downward (e.g., to reverse or overcome the bias of springs 197 under lock ring 193, and springs 297 under lock 192), releasing catch 262 from gears 293; and releasing threads 320 from threads 220. Thus, shaft 174 may move distally or proximally if knob 130 or distal housing 120 is pulled away AW or pushed towards FO T-handle 169 (e.g., without needing to rotate knob 130). FIG. 1G may show shaft 174 moved proximally, such a by pulling knob 130 when switch 171 is in the release position. In some embodiments, when in the release position, switch 171 allows shaft 174 and plunger seal 110 to move freely in response to a "back pressure" of fluid in the syringe (e.g. from an occlusion balloon). When in the release position, switch 171 may allow shaft 174 and plunger seal 110 to move freely within syringe barrel 112 in response to a rotational or longitudinal forces or displacements applied by the user to the knob 130 (as well as to any part of distal housing 120). According to embodiments, this release position 202 allows the user to most easily perform at least one of: fill the inflation deflation device 100 with fluid, remove air from the inflation deflation device 100, aspirate a mechanical pressure gauge and fill any attached fluid lines with fluid using device 100. It is preferred that latch 150 be in the occlusion position during these functions of device 100 (when switch 171 is in the release position) and prior to any use of device 100 to inflate an occlusion balloon. These preferences may avoid causing annoying the operator and/or causing dysfunction of the device 100. Such dysfunction may cause a treatment to fail and/or an injury to the vessel of a patient being treated, such as due to an unexpected change in pressure in device 100 resulting from any of these functions.

When lever 240 is moved into adjust position 204, bottom 250 may have a protrusion that press on platform PL2 with sufficient force/displacement to cause it to move downward (e.g., to reverse or overcome the bias of springs 197 under lock ring 193), releasing catch 262 from gears 293. When lever 240 is moved into adjust position 204, bottom 250 may have a recess (lack of a protrusion or other configuration) that allows platform PL1 to be biased by springs 297 under lock 192 so that threads 320 engage threads 220. Thus, when in adjust position, switch 171 may allow shaft 174 to move distally or proximally by rotating knob 130 or distal housing 120. FIG. 1G may also show shaft 174 moved proximally, such a by rotating knob 130 counter-clockwise when switch 171 is in the adjust position. In some embodiments, when in the adjust position, shaft 174 and plunger seal 110 will not move in response to a "back pressure" of fluid in the syringe (e.g. from an occlusion balloon). The adjust position is the preferred position for using device 100 to inflate the balloon until it attains the desired occlusion (or inflation condition). However; because the knob 130 or distal housing 120 may be inadvertently rotated by the operator, by setting device 100 aside or subsequent operation of latch 150, it is not preferred that the adjust position be retained after the initial occlusion is attained. Once the desired occlusion (or balloon inflation condition) is attained, it is preferred that the switch be moved to the lock position, as will be described later. These preferences may avoid causing annoying the operator and/or causing dysfunction of the device 100. Such dysfunction may cause a treatment to fail and/or an injury to the vessel of a patient being treated, due to an unexpected change in pressure in device 100 that may result from using other positions.

When in the adjust position, switch 171 may allow shaft 174 and plunger seal 110 to move to a plurality of rotational positions in response to rotational force or displacement ROTS applied to knob 130 or distal housing 120 by the operator, but prevents the plunger from moving in response to pressure applied to a head of the plunger. In some embodiments, plunger seal 110 may be moved (by rotating knob 130 or distal housing 120) to locations along length L of syringe barrel 112 that cause equal volumes to be output by the syringe barrel 212 when the syringe is filled with a liquid. In other embodiments, plunger seal 110 may be moved (by rotating knob 130 or distal housing 120) to locations along length L of syringe barrel 112 to adjust the pressure to be output by the fluid within syringe barrel 112 (the fluid in communication with the balloon) when the syringe is filled with fluid.

When lever 240 is moved into lock position 206, bottom 250 may have a recess (lack of a protrusion or other configuration) that allows platform PL2 to be biased by springs 197 under lock ring 193 so that catch 262 engages gears 293. When lever 240 is moved into lock position 206, bottom 250 may have a recess (or lack of a protrusion) that allows platform PL1 to be biased by springs 297 under lock 192 so that threads 320 engage threads 220. Thus, shaft 174 may be prohibited from rotating (e.g., due to engagements 260 of lock ring 293 being locked into slots 194 of the shaft), and may be prohibited from moving distally or proximally (e.g., shaft 174 can not be moved by rotating knob 130, or otherwise). FIG. 1G may also show shaft 174 locked in a proximal position, such that shaft 174 can not be moved by rotating knob 130, when switch 171 is in the lock position. In some embodiments, when in the lock position, shaft 174 and plunger seal 110 will not move in response to a "back pressure" of fluid in the syringe (e.g. from an occlusion balloon). In some embodiments, switch 171 may be described as a rotational lock because in the lock position, switch 171 (e.g., lock 192, lock ring 193, and gear 196) lock the rotation and location of shaft 174 (and thus lock plunger seal 110) into a position or location along length L to ensure that the plunger is locked at a position (e.g., without rotation or being moved by a "back pressure" of fluid in the syringe (e.g. from an occlusion balloon)). The lock position is the preferred position for the operation of latch 150 to deflate and then re-inflate the balloon (to its original inflation condition).

Switch 171 may be moved between positions by moving lever 240 extending through window 141 (e.g., the lever is moved by a user between three positions within the window). In some embodiments, switch 171 may be moved by a user manipulating lever 240 between release position 202, adjust position 204, and lock position 206, wherein the lock position is adjacent to the adjust position. Thus, the user may move the switch from the lock position to the adjust position, and vice versa. It is considered that the user may also move the switch from the lock position to the release position, and vice versa; or from the release position to the adjust position, and vice versa. It is preferred that the adjust and lock positions be designed to be adjacent so that, once the occlusion is attained (balloon volume or pressure is adjusted) in the adjust position, the switch 171 may be moved to the lock position without the switch 171 having to go through the release position. If the switch 171 was required to go through the release position, the shaft 174 would become free of constraints and would move in response to the pressure in the syringe barrel 112, causing the loss of the occlusion and the loss of the ability to use latch 150 to re-inflate the balloon to an occlusive condition after the use of latch 150 to deflate the balloon.

In preferred embodiments, the release position is not between the lock and adjust positions. Thus, the user is not able to move the switch from the lock position to the release position, and then to the adjust position, and vice versa. Instead, switch 171 can be transitioned between the adjust position and the locked position without entering the release position. In preferred embodiments, the switch comprises a single switch having the adjust position located between the release position and the locked position, or the locked position located between the release position and the adjust position.

FIGS. 2A-2F are schematic partial see through views of various components of a second embodiment of an inflation deflation device. In some embodiments, various components of FIGS. 2A-2G may be similar to correspondingly numbered parts of FIGS. 1A-2G.

Figure 2A:
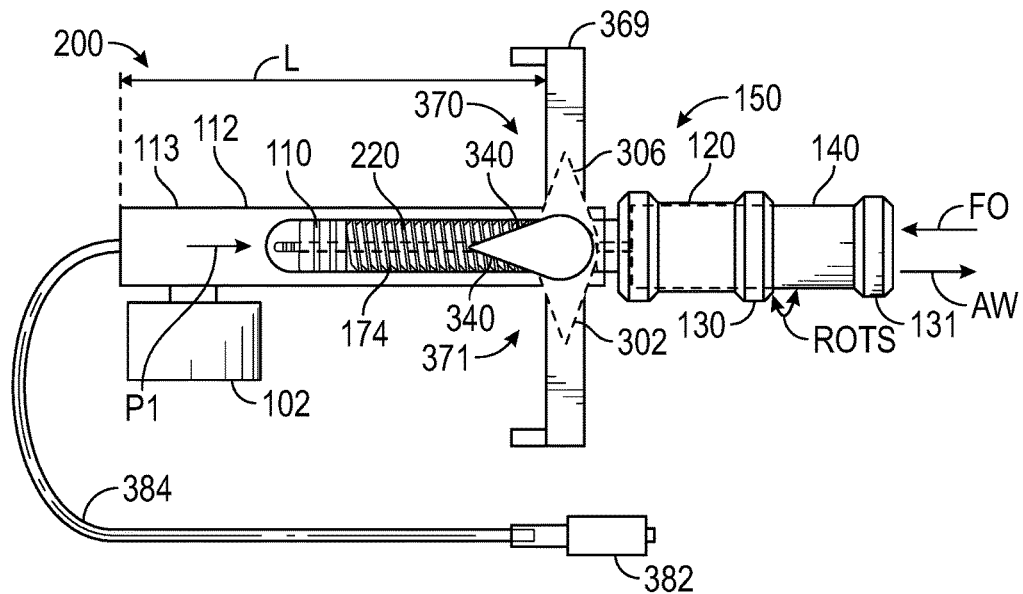
FIGS. 2A-2G are schematic partial see through views of various components of a second embodiment of an inflation deflation device.

FIG. 2A shows inflation deflation device 200 having proximal end 106 and distal end 104. Device 200 has knob 131 attached to proximal housing 140 and rotational knob 130 attached to distal housing 120. Proximal housing 140 is positioned relative to distal housing 120 by releasable latch 150. Distal housing 120 is attached to syringe barrel 112 having plunger seal 110 disposed there within and having syringe tip 113. Extension line 384 is in fluid communication with the inside of syringe barrel 112 and attached to tip 113. Extension line 384 is also in fluid communication with and attached to luer 382, such as a luer to attach to and put device 200 in fluid communication with a catheter and an occlusion device or balloon. Plunger seal 110 is coupled by shaft 174 to screw mechanism 370 and three position switch 371. Screw mechanism 370, switch 371, and syringe barrel 112 are housed within T handle 369. T handle 369 may have a window similar to window 175 of FIG. 1A. Gauge 102 is shown mounted on T handle 369 and is in fluid communication with the inside of syringe barrel 112. Proximal housing 140 is coupled to a shaft 274 and plunger (e.g., seal 210) within shaft 174 and in fluid communication with the inside of syringe barrel 112.

Syringe barrel 112 may have length L, and location L1 and L2. T handle 369 may include halves, fasteners, springs and other components as noted for handle 169. Various components of device 200 function similar to and/or may be made of various materials as described for device 100.

Figure 2B:
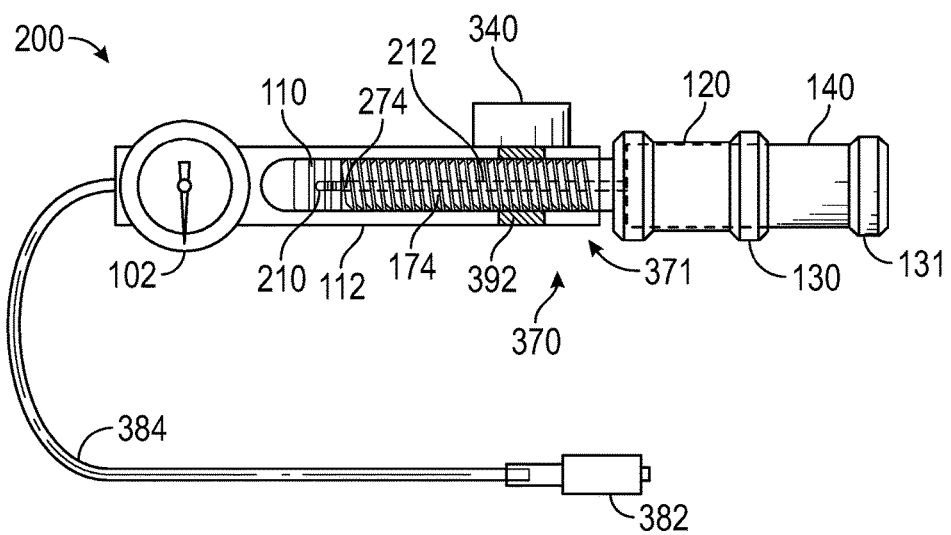
Figure 2C:
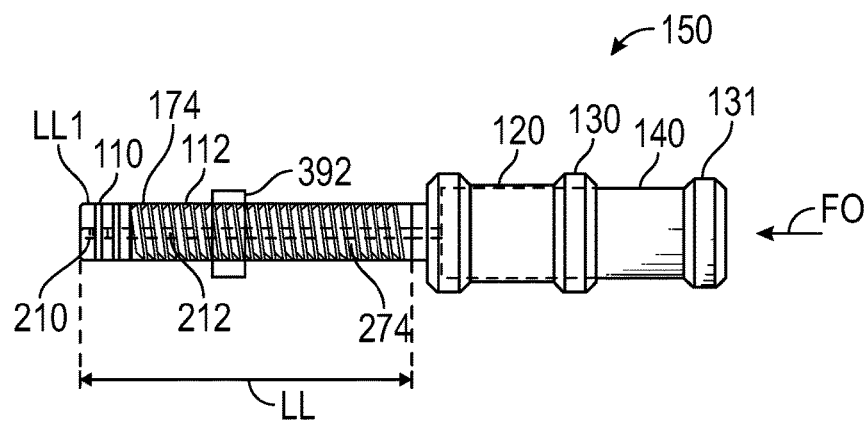

FIG. 2B shows switch 371 including lever 340; lock or latch portion 392; and shaft 174 (which may all be mounted within T handle 369). The components of switch 371 may be included in screw mechanism 370. Lock 392 may be mounted on springs (e.g., such as springs 297 shown within mount 199 of FIG. 1) to bias lock 392 upwards, or away from the bottom of handle 369.

Screw mechanism 370 may include components similar to and/or may function similar to mechanism 170 for moving shaft 174 and plunger seal 110 along length L of syringe barrel 112 when the switch 371 is in the adjust position. Specifically, when knob 130 is rotated in direction ROTS the screw mechanism moves plunger seal 110 along length L within syringe barrel 112. In some embodiments, screw mechanism 370 includes a plurality of incremental volume positions as noted for mechanism 170.

Switch 371 may also include rotational positions for lever 340, such as positions separated by 90 degrees around a rotation axis of lever 340. It can be appreciated that the positions can be separated by other rotational amounts around axis of lever 340, such as by equal or unequal amounts in rotation. Lever 340 may be movable, by a user, between three positions within the rotational limits of lever 340 (e.g., such as within a total of 180 degrees). Moving the lever may cause switch 371 to be moved between three positions (e.g., from one position to an adjacent position) by a user (e.g., a surgeon). Switch 371 may have lock position 306 to ensure that the plunger (e.g. large plunger seal 110) can be locked at a position so it will not rotate accidently or incidentally or be moved by a "back pressure" of fluid in the syringe (e.g. from an occlusion balloon). Switch 371 may have release or "release" position 302 to allow plunger seal 110 to move in response to such back pressure or in response to a user pushing, pulling or turning a knob attached to a shaft of the plunger seal. Switch 371 may also have adjust position 304 that prohibits the plunger seal from moving in response to a back pressure, but allows the plunger seal 110 to be moved to increase the pressure within syringe barrel 112 and/or to expel a volume of fluid from inside syringe barrel 112 when user rotates knob 130. In preferred embodiments the adjust and lock positions are adjacent so that the switch can be moved between the adjust and locked positions without encountering the release position.

The difference between screw mechanism 370 and screw mechanism 170 is that there is no biased gear (196) or ring lock (193) in screw mechanism 370 and lock 392 has its threads (320) on the top of lock 392. Additionally, slots 194 are not a required feature of screw mechanism 370.

Similar to device 100, device 200 may include proximal housing 140 having indexing locks 152 on an outer perimeter of proximal housing 140, such as for engaging internal recesses or stops of distal housing 120. Thus, movement of the housing away AW and towards FO each other may be constrained by locks 152 engaging recesses (e.g., recesses 182 and 184); and/or by stops 189 and 190 as described for device 100. Knob 130 may be mounted in or attached to distal housing 120.

Screw mechanism 370 doesn't require the inclusion of slots 194 in threads 220 of shaft 174, as the mechanism to assure the locking of shaft 174 is different from that of device 100. Base 246 couples proximal housing 140 to internal shaft 274, which resides or is disposed within second syringe barrel 212 of internal shaft 274. FIG. 2 shows plunger seal 110 including one or more o-rings to be mounted on shaft 174, such as described for FIG. 1.

According to embodiments, internal shaft 274, syringe barrel 212, knob 131 and syringe barrel 112 may include components and/or function as describe for FIG. 1. Thus, proximal housing 140 and distal housing 120 may rotate with respect to handle 169, thus allowing rotation of knob 130 to cause screw mechanism 170 to move shaft 174 (and 274) and plunger seals 110 (and 210) along length L (and LL) of syringe barrel 112 with lever 340 in the adjust position.

Releasable latch 150 of device 200 may function similar to that of device 100. Thus, when knob 131 is pulled away from distal housing 120 (e.g., see FIG. 2E) latch 150 may be put in a perfusion position, and when pushed towards distal housing 120 (e.g., see FIG. 2C) latch 150 may be put in an occlusion position.

FIGS. 2C-2G show internal shaft 274 having internal plunger seal 210, such as a plunger to form a liquid tight seal within second syringe barrel 212. Thus, plunger seal 210 may be moved along length LL within second syringe barrel 212 which may be a cylindrical shaped opening formed through the inside of shaft 174 (e.g., see FIG. 2F). Indexing locks (e.g., similar to locks 152) may be disposed within openings in housing 140.

Gauge 102 may be a pressure gauge to measure the pressure within the syringe barrel 112 and in the system proximal to the catheter, similar to that of FIG. 1.

According to embodiments, releasable latch 150, housing 140, housing 120, syringe barrel 112, shaft 174, syringe barrel 212, plunger seal 110, knob 131 and rotating knob 130 all function (e.g., move plunger seal 110 along length L and plunger seal 210 along length LL) similar to the description of FIG. 1. However, switch 371 in conjunction with lock 392 functions differently than switch 171 (and thus mechanism 370 which includes switch 371 functions differently than mechanism 170 which includes switch 171).

Figure 2D:
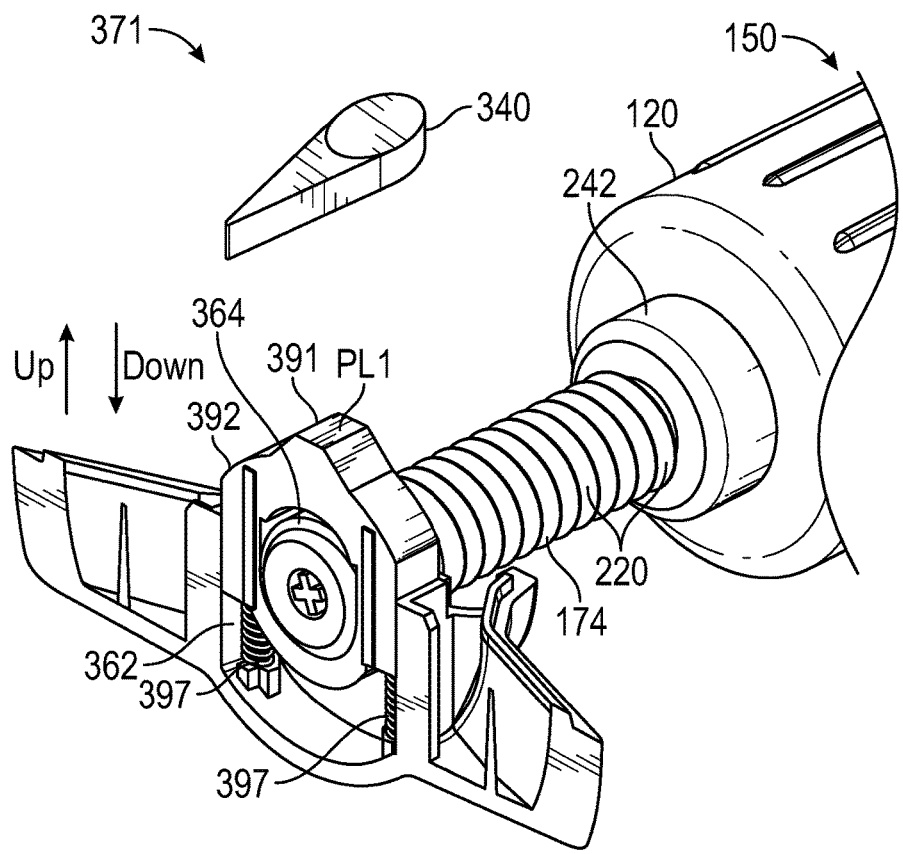

As shown in FIGS. 2A-2G show details of switch 371. For example, as shown in FIG. 2D switch 371 includes lock 392, which may disengage, engage or lock the position of threads 220 of shaft 174 depending upon the position of lever 340. The lock 392 is wider than shaft 174 and may be made of high friction material, like ionomer. The position selection mechanism (e.g., lever 340) may include an inclined or threaded, detented and spring loaded mechanism 391 that pushes lock portion 392 to engage threads 220 as lever 340 is moved from the release position to the adjust position and from the adjust position to the lock position.

In "RELEASE" or release position 302 or with lever 340 turned toward "release", through hole 362 of the latch portion has an ID large enough to let the shaft 174 and threads 220 to pass through it unimpeded, but small enough that the distal end of the shaft 174 construction will not pass through it (the shaft 174 portion that mounts plunger seal 110 may be attached to shaft 174 after lock 392 is positioned over shaft 174). In "RELEASE" position, lock 392 is biased up by springs 397, such as springs 197 of FIG. 1 and stopped by the underside of lever 340 (e.g., or components thereof) or by other device 200 components to an upper position (e.g., "up"), such that threads 364 at the top of lock portion 392 do not engage threads 220 of shaft 174.

In its "ADJUST" position 304, or with lever 340 turned toward "adjust", lock 392 is pushed down or otherwise biased by lever 340 (e.g., or components thereof) to a first depressed position such that threads 364 at the top of lock portion 392 engage threads 220 of shaft 174. In some cases, lever 340 may be similar to lever 240. In some cases, lever 340 may have a rotating vertical screw design, such as with threads around the outer perimeter of a shaft extending from the bottom of the part of lever 240 grasped by the operator. Those threads may engage opposing threads around the inner perimeter of the opening in the handle that lever 340 extends through. The bottom of lever 340, within the handle may have a surface (e.g., similar to bottom 250) that engages the top platform PL1 of mechanism 391, pushing it downward against the spring force, or allowing it to be pushed upwards by the springs until mechanism 391 contacts the surface. The first position may describe an amount of force applied by threads 364 to threads 220 that allows shaft 174 to rotate relative to handle 369 so that screw mechanism 370 moves plunger seal 110 along length L within syringe barrel 112. In some embodiments, when in the adjust position, shaft 174 and plunger seal 110 will not spontaneously move in response to a "back pressure" of fluid in the syringe (e.g. from an occlusion balloon).

In its "LOCK" position 306, lock 392 is further pushed down or otherwise biased by lever 340 (e.g., or components thereof) to a second depressed position or such that threads 364 at the top of lock portion 392 very firmly engage or lock into position, threads 220 of shaft 174. The second position may describe an increased amount of force applied by threads 364 to threads 220 that prohibits shaft 174 from rotating relative to handle 369 so that screw mechanism 370 can not move plunger seal 110 along length L accidently/incidentally as a result of inadvertent forces applied by the user or as a result of operating the releasable latch 150. The second position may describe a downward, spring, thread or incline determined force that introduces enough friction between threads 364 and threads 220 on shaft 174, so that plunger seal 110 is effectively locked in position (housings 140 or 130 or knobs 130 or 131 can not be easily rotated by the user) relative to length L of syringe barrel 112. In preferred embodiments, when in the adjust position, shaft 174 and plunger seal 110 will not spontaneously move in response to a "back pressure" of fluid in the syringe (e.g. from an occlusion balloon). In some cases, as compared to device 100, device 200 provides a more simple and efficient design. For instance, device 200 does not require slots 194 or lock ring 193 to engage those slots. Thus, device 200 has fewer components and fewer points of failure. It may also be produced at a lower cost.

Figure 2E:
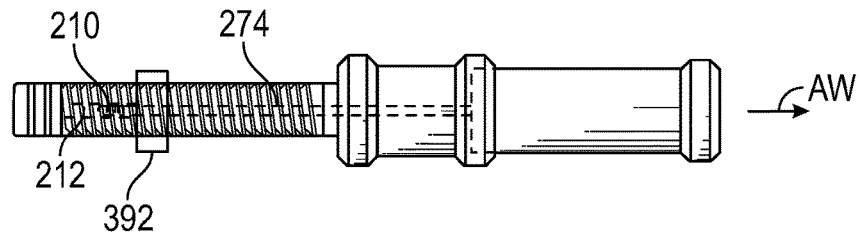
Figure 2F:
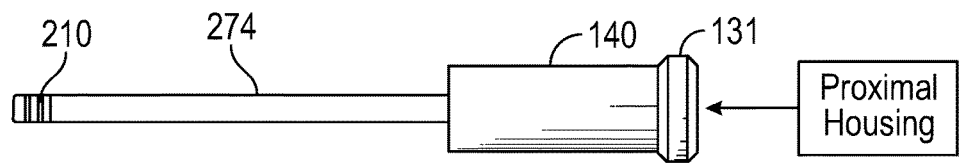
Figure 2G:
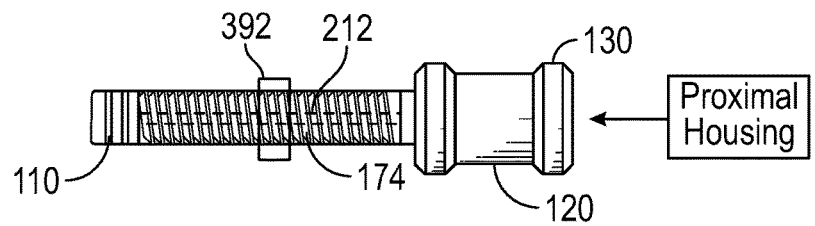

For example, FIG. 2E may show shaft 274 moved proximally (e.g., from the distal position shown in FIG. 2C), such a by pulling knob 131 in direction AW relative to housing 120 to put latch 150 in the perfusion position (e.g., from occlusion position of FIG. 2C), while switch 371 is in the lock position 306. It can be appreciated that after FIG. 2E, FIG. 2C may show shaft 274 moved distally (e.g., from the proximal position shown in FIG. 2E), such a by pushing knob 131 in direction FO relative to housing 120 to put latch 150 in occlusion position (e.g., to occlusion position of FIG. 2C), while switch 371 is in the lock position 306.

Screw mechanism 370 and latch 150 of device 200 may function similar to screw mechanism 170 and latch 150 of device 100, such as to cause plunger seal 110 and/or plunger seal 210 to be located along the length of the syringe barrel 112 and/or syringe barrel 212 to define a plurality of position locations. In some embodiments, plunger seal 110 and screw mechanism 370 may be configured to increase a pressure of fluid in syringe barrel 112 to a pressure to cause a balloon to occlude a human blood vessel, and plunger seal 210 and releasable latch 150 may be configured to translate plunger seal 210 from an occlusion position, to a first latched position to cause perfusion (e.g., by pulling knob 131 relative to housing 120) and then to the second latched position to cause re-occlusion of the blood vessel (e.g., then by pushing knob 131 relative to housing 120). In other embodiments, plunger seal 110 and screw mechanism 370 may be configured to incrementally decrease the volume of fluid in syringe barrel 112 to incrementally inject volumes of fluid into a balloon to occlude a human blood vessel, and plunger seal 210 and releasable latch 150 may be configured to translate plunger seal 210 from an occlusion position, to a first latched position to cause perfusion (e.g., by pulling knob 131 relative to housing 120) and then to the second latched position to cause re-occlusion of the blood vessel (e.g., then by pushing knob 131 relative to housing 120).

Switch 371 may be moved between positions by rotating lever 340 (e.g., the lever is rotated by a user between three positions). In some embodiments, switch 371 may be rotated by a user manipulating lever 340 between release position 302, adjust position 304, and lock position 306, wherein the lock position is adjacent to the adjust position. Thus, the locations of positions 302, 304 and 306 relative to each other may be similar to the locations of positions 102, 104 and 106 described for FIG. 1.

According to embodiments, for devices 100 and 200, the latch "RELEASE" position operates to allow the ICVI to be filled and aspirated (remove air from the syringe, pressure gauge and extension line) and then the "ADJUST" position is used to inflate the occlusion balloons to an occlusive OD or configuration by use of pressure steps or volume increments. The latch "LOCK" position is used to securely lock the position of the plunger seals 110 relative to the syringe barrel 112 once occlusion has been obtained so that accidental/inadvertent forces and/or the use of the releasable latch 150 for balloon deflation (perfusion) and re-inflation (re-occlusion) will not cause the inflation volume required for occlusion and set during the initial occlusion to be changed.

One advantage of having the release position is to be able to easily aspirate device 100 or 200 (e.g., and the system including inflation lumen and occlusion balloon) prior to use or prior to treatment of a treatment or target region. In other words, device 100 or 200, in the release position, may be used like a normal syringe to aspirate the catheter, the device 100 or 200 and other parts of the system and thus, assure that all parts of the system are filled with fluid and that the balloon is deflated prior to insertion into the body. An occlusion balloon not in fluid communication with/not connected to device 100 or 200 may then be most easily positioned at the desired position in the vasculature. The switch may then be moved to the adjust position, and the knob/housing rotated to assure that the device has only fluid at its connection to the catheter/system and then, be "wet" connected to the catheter/system without introducing air. Next, the pressure (or in some embodiments, the volume increments) of the device may be adjusted (knob 130 or housing 120 may be rotated to increase pressure (or rotationally incremented to inject fluid volumes into the balloon) until vessel occlusion is attained. Once occlusion is attained, the switch may be moved to an adjacent position, the lock position, to lock the device (e.g., and system) at the occlusion volume, without transitioning to the release position (and releasing the occlusion volume setting). Once in the lock position, the device (e.g., and system) may hold or maintain an amount of volume in the system to maintain the occlusion. This occlusion volume may be maintained during treatment of a target region of a vessel or tissue fed or drained by the vessel, such as by infusion of a treatment agent or drug. Moreover, the occlusion may be released (for perfusion) and quickly re-established after perfusion periods between multiple infusions of the same target region during a treatment, such as periods when latch 150 is transitioned from the perfuse position to the occlude position. Such periodic perfusion avoids ischemia and other damage to the treatment region during a treatment (e.g., such as noted herein).

Furthermore, if it is determined that the occlusion had not been sufficiently established and it is desired to increase the occlusion pressure or volume (e.g., by a predetermined amount) prior to a treatment, during occlusion, during treatment, or after transition of latch 150 to back to the occlusion position, the switch can be moved from the lock position to the adjacent adjust position, and knob 130 rotated to increase pressure or injected volume, without transitioning to the release position (and releasing the original occlusion volume, requiring a more significant (time consuming) procedure to re-establish the occlusion).

For instance, device 100 or 200 may be a low pressure (for instance, with a 4 ATM Max. reading or less pressure gauge 102) balloon inflation-deflation device, an Indeflator®. As demonstrated during experiments and an analysis of fits, areas, volumes and flows, a 4.0 mm compliant balloon may be deflated from its maximum OD (5.0 mm, and nearly spherical) by a device 100 or 200 that is fabricated with a 3/16 inch second syringe ID and a standard o-ring (size AS-568-003) on the distal end of the internal plunger (e.g., seal 210) with a 1.5" throw between the inflation and deflation positions will produce enough vacuum (change in system volume) in an LP-60 (an Abbott Vascular Low-Pressure Indeflator®, 60 PSI [about 4 ATM] Max. pressure gauge reading, using a mechanical pressure gauge) based design (both device 100 and 200 are LP-60 based designs) to deflate the balloon in about 4-5 seconds. Additionally, internal plunger (e.g., seal) forces will be produced during perfusion and re-occlusion of that balloon such that using a latch 150 that resists at least 6 ATM at re-occlusion (after move to inflation position) and at least 1.5 ATM at perfusion (after move to deflation position) will result in the latch 150 remaining in either latched condition immediately after the transition.

Device 100 or 200 may be syringe assembly with a pressure gauge, an extension line with a rotating male Luer on its distal end and a means to control the plunger (e.g., seal) of the syringe (e.g., screw mechanisms, switches, latches and knobs described above for device 100 or 200). Syringe barrels 112, 212, tip 113, and extension line and/or luer of device 100 or 200 may put those devices in fluid communication with a balloon to occlude and perfuse a blood vessel. The balloon may be coupled to device 100 or 200 using a catheter having a lumen for communicating fluid there between. Such an assembly may be described as a system.

For instance, device 100 or 200 may be designed to safely inflate a balloon to an OD just sufficient to occlude a vessel (allow for treatment of the occluded blood vessel region), to deflate the balloon (to perfuse blood and/or treatment agent from the region), to easily and repeatedly re-inflate the balloon to the same safe occlusive OD, and then deflate the balloon. The repeated re-inflation of the balloon to the same safe occlusive OD may be accomplished by returning the syringe volume to the same volume it was adjusted to when the safe occlusive OD was originally attained. The ICVI's syringe volume may be controlled to both accomplish the initial occlusion and the repeated re-inflation/deflation cycle, hence the ICVI name. The ICVI may be a one-time use device that is qualified to be EtO sterilized twice. In some embodiments, device 100 or 200 may be used in processes described below for FIG. 3-5.

Figure 4:
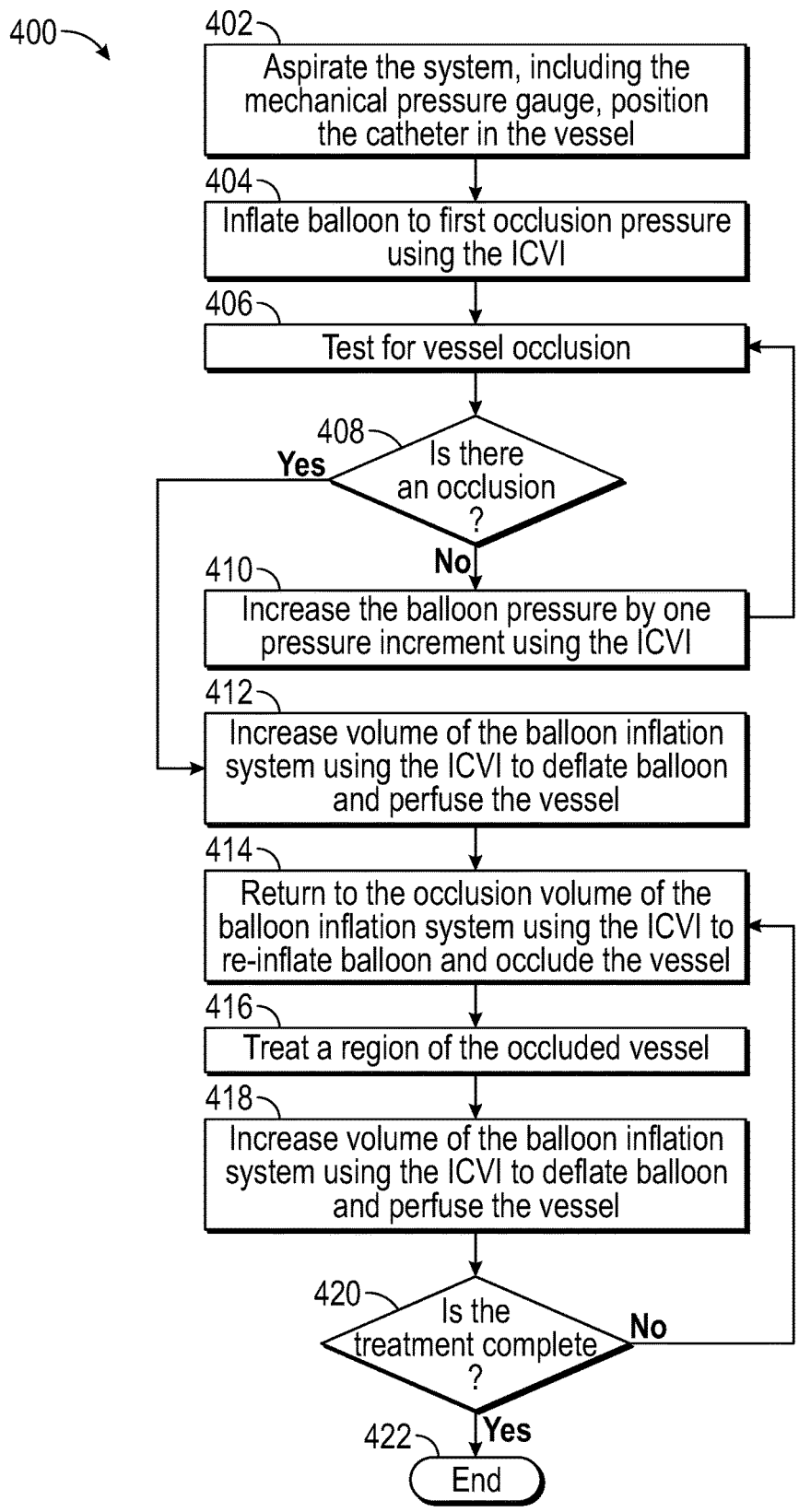
FIG. 4 is a flow diagram of a process to inflate a balloon to occlude a blood vessel, to perfuse the vessel, and to treat an occluded region.

At this point, it may be worth describing occlusion balloon function and how the choices one makes in designing the occlusion functioning of an occlusion balloon affects how an Indeflator® may be safely used to attain the initial occlusion and the trade-offs of occlusion balloon design. The descriptions farther below for FIG. 4 provide some specific examples of such possible uses. The larger the nominal OD of a spherical occlusion balloon or the length of a more cylindrical occlusion balloon (all other factors being equal or proportional), the greater its volume and thus, the longer it will take to initially inflate, deflate and re-inflate the balloon. Nominal OD may be defined as the balloon OD when the balloon is inflated with the first occlusion pressure, such as described herein. As noted further below, in some cases, this may be true for compliant and non-compliant balloons. Physicians generally do not like the idea of unnecessarily longer initial inflation, deflation and re-inflation times (due to increased procedure time and ischemia reasons) and thus, most often prefer to use the smallest nominal OD/shortest length balloon that will occlude the vessel being treated. Thus, compliant occlusion balloons with various nominal OD's and/or lengths are often demanded by physicians and provided by medical device manufacturers. However, the ability of the most common/most available method, angiography, to measure the ID of the vessel, especially diseased vessels, is imprecise, often incorrect by 0.5 mm or more. (Note, due to vessel disease, most vessel ID's are not circular, which is why angiography, a 2D shadow-like imaging modality, is imprecise. Thus, what is really being compared in the descriptions below is the OD perimeter of the balloon and the ID perimeter of the vessel, however; to keep the descriptions simpler, the descriptions will continue to refer to OD's and ID's.) Thus, according to some embodiments, there may be two conditions under which the initial occlusion may be performed. The first condition is when the chosen nominal balloon OD is greater than or equal to the ID of the vessel. The second condition is when the chosen nominal balloon OD is less than the ID of the vessel. Since non-compliant balloons should not have their OD's effectively adjusted (the definition of a non-compliant balloon), non-compliant balloons should not be used to occlude a vessel in the second condition. Thus, non-compliant balloon occlusion systems should have their nominal balloon OD's equal to or greater than the vessel ID that they must occlude.

In the first condition, when initially inflating a compliant or non-compliant balloon using pressure control (an elastic balloon requires volume control), at occlusion the balloon is in perimeter contact with the vessel and is very likely to have a fold or folds and an irregular shape. In this case, the minimum required occlusion pressure in the balloon may be the pressure required to inflate the balloon into contact with the vessel wall (overcome blood pressure) plus the pressure required to press any folds in the balloon together (e.g., effectively force the wrinkles out of the balloon material) or cause the balloon to conform to the vessel wall to prevent a leakage path through the balloon fold(s) or bends in the vessel wall (overcome balloon flexural modulus). This is called the first occlusion pressure. Any extra pressure inside the balloon must be supported by/applied to the vessel wall. Additionally, balloons mounted on catheters may be folded to facilitate their insertion into the body/vessel, and may require a higher pressure than the first occlusion pressure to initially unfold the balloon. Additionally, if the physician was to inflate the balloon to the first occlusion pressure by applying the first occlusion pressure (a low pressure) via the Indeflator®, then, due to catheter inflation lumen flow resistance, the time required to inflate the balloon would be quite long and could be annoying to the physician. The first occlusion pressure may be estimated for a balloon, such as based on testing of similar balloons, as noted below.

Thus, when initially inflating the compliant or non-compliant balloon using pressure control to attain the initial occlusion, the physician may be instructed to place the device lever into the adjust position and to turn the knob of the device (adjusts the syringe/proximal system volume) at a rate required to create/observe a pressure of about 1 ATM on the gauge and to continue turning until the rate of turning required decreases noticeably and then to turn the knob, as required, to adjust the pressure reading to a specified first occlusion pressure for a short time until the pressure reading stabilizes. This procedure allows the balloon to be inflated much more rapidly and limits the amount of pressure that can be applied to the vessel wall, preventing vessel damage due to over stretching it. At the beginning of this procedure, there is very little pressure inside the balloon, so the fluid flow rate down the balloon inflation lumen is maximized and the latch (e.g., knob) usually needs to be turned rapidly to maintain the about 1 ATM reading on the gauge. As the balloon inflates, it must overcome its own flexural modulus and blood pressure and then begins to apply increasing pressure against the vessel wall to start to occlude the vessel, and thus, the pressure inside the balloon increases. This balloon pressure increase causes less of a pressure drop across the balloon inflation lumen, which causes the fluid flow rate down the balloon inflation lumen to decrease and thus, the knob usually needs to be turned less rapidly to maintain the about 1 ATM reading on the gauge. As a practical matter, due to the time it takes the physician to initially reach the about 1 ATM reading, in some cases it is only the balloon pressure increase due to the contact of the balloon with the vessel wall that can be detected by the decreased turning rate of the latch. For instance, when the pressure in the balloon reached about 0.50-0.75 ATM in tested occlusion balloons, the required turning rate of the latch (e.g., knob) may drop to about half or less of its initial value, which was easily detected by the user. It should be noted that, although the pressure inside the balloon may be 0.50-0.75 ATM, the additional pressure that the balloon can apply to the vessel wall should be less by the sum of the blood pressure and the pressure required to overcome the flexural modulus of the balloon during inflation.

One standard method for testing for an occlusion is to inject contrast down another lumen of the catheter or down another catheter (such as a guide catheter) and observe the wash out, if any, of the contrast under fluoroscopy. If the physician had chosen a balloon nominal OD that is too small (due to vessel measurement errors) to occlude the vessel at the first occlusion pressure (the actual vessel ID is greater than the balloon's nominal OD), then when the vessel is tested for occlusion, there will be no occlusion and the initial occlusion may be attained in the second condition. Alternatively, the physician could deflate the balloon, remove the catheter and replace it with a catheter that has a larger nominal balloon OD, which is the only alternative for a non-compliant balloon. Since replacing the catheter is expensive and requires additional steps and therefore, more procedure time, this is not the preferred method and thus, non-compliant occlusion balloons are not preferred in occlusion system designs that the second condition is a significant possibility. In the second condition, attaining the initial occlusion, using pressure control, may be to increase the gauge pressure (and thus, the increasing the pressure inside the balloon and the balloon OD), in increments until the vessel occlusion test indicates that an occlusion has been attained. Since the second condition also requires extra steps, the physician may be requested by the device manufacturer to choose a balloon size that exceeds the measured ID of the vessel by 0.5 mm, 1.0 mm or more and thus, most often, the physician may avoid the necessity of obtaining the initial occlusion in the second condition and thus, avoid becoming annoyed. The pressure increment values are chosen to increment the OD of the balloon in steps that will not cause significantly damage to the vessel. For instance, in general, coronary arteries 2.0 mm in ID and over may be stretched as much as 30% without significant damage. In preferred embodiments, the first pressure increment of the second condition (e.g., inflation to greater than the first occlusion pressure) may be chosen to be a pressure increase (e.g., of about 0.25 ATM or less) to safely limit the pressure that may be applied to the vessel wall in the case where the vessel is mistakenly thought to not be occluded or is almost fully occluded at the first occlusion pressure and the vessel ID is less than or equal to the nominal balloon OD. In some embodiments, the Max. pressure that the balloon is rated to be inflated to is limited (by instructions to the physician) to the relatively elastic region of the compliant balloon material (region without rapid creep at body temperature).

Figure 5:
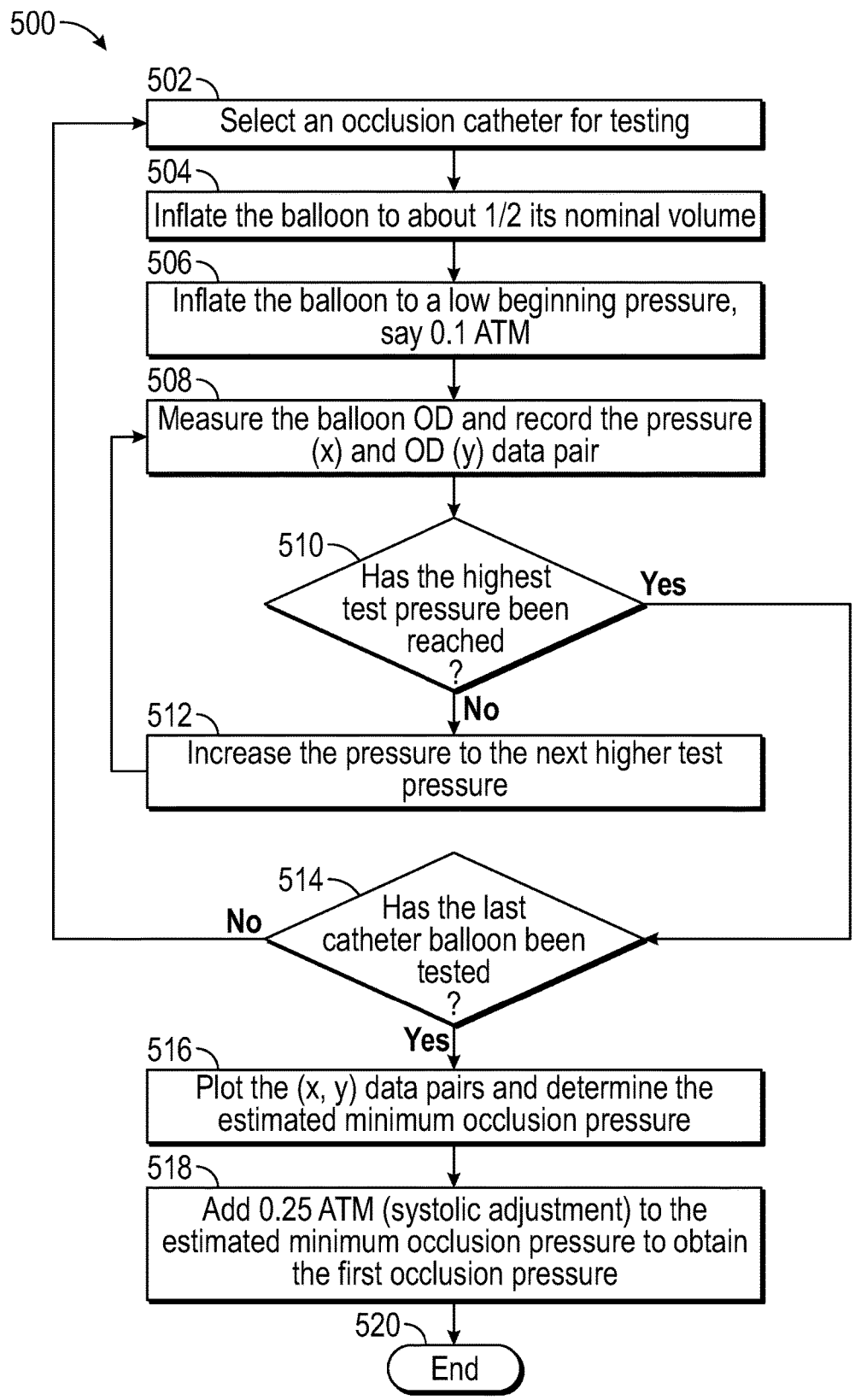
FIG. 5 is a flow diagram of a process to estimate a first occlusion pressure of a type of balloon.

The first occlusion pressure of a balloon may be determined from testing using a test set-up to simulate the vessel(s) or may be calculated by a procedure that involves measuring the OD of the balloon at increasing pressures in a bath at body temperature. The descriptions farther below for FIG. 5 provide some specific examples of such determining and calculating. Since the OD's of the balloon at increasing pressures may be tested to determine the pressure increments of the second condition, calculating the first occlusion pressure is one preferred method. It should be noted that modern balloon manufacturers are typically able to consistently fabricate balloons that have their nominal OD's and pressure responses within a suitably narrow range and thus, it is not usually necessary to test each balloon prior to its use; it is usually only necessary to test each balloon's design and processing limits. The minimum first occlusion pressure of a balloon design is the pressure at which the balloon attains a substantially circular cross-section, within a predetermined limit. A typical pre-determined limit for a coronary occlusion balloon is a difference in balloon diameter of less than or equal to 0.1 mm, when the balloon diameter is measured on many different axes at the same time and at each test pressure. If one is measuring pressure-diameter data pairs of many balloons of the same design on a single diameter axis, then it is not necessary to actually measure the balloon diameters on multiple axes simultaneously. One may estimate the minimum first occlusion pressure by setting it at the largest ending pressure at which some of the measured balloon diameters decrease or stay equal when their pressure is increased (requires the balloon to be partially inflated [for instance, ½ inflated by volume] and then small inflation pressure steps applied at the lower test pressures). At this point, any folds may have been forced out of the balloon. Another way to estimate the minimum first occlusion pressure is to plot the pressure (x)-diameter (y) data pairs of this data and perform a standard linear regression analysis. At the higher pressures, the data points will cluster near a straight line (the linear regression line). However, when you examine the curve at the lower pressures, the data points will begin to distribute themselves much further away from this straight line. The pressure at which the data points begin to distribute themselves further away from this straight line is the estimated minimum first occlusion pressure.

Figure 3A:
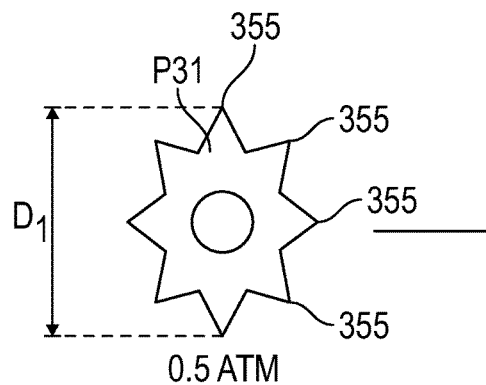
FIG. 3A shows an occlusion balloon having folds when inflated with pressure below a first occlusion pressure.
Figure 3B:
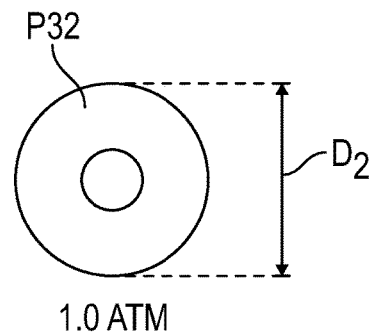
FIG. 3B shows an occlusion balloon having a substantially circular cross-section when inflated with pressure at or above a first occlusion pressure.

A drop or little or no change in measured balloon diameter with an increase in balloon pressure seems counterintuitive, but it may occur in many practical compliant and non-compliant occlusion balloon designs, for embodiments having the balloon folded on the catheter shaft to aid in balloon placement in the vessel. As a result of the balloon being folded, the balloon material may be set into a wrinkled condition. FIGS. 3A and 3B are exaggerated illustrations to help show an example of how this effect can occur. FIG. 3A shows an occlusion balloon which had been folded and then is inflated with pressure below that required to overcome the flexural modulus of the folded balloon material and thus, the OD of the balloon is not very circular. FIG. 3B shows the same occlusion balloon having a substantially circular cross-section when inflated with pressure at or above the pressure required to overcome the flexural modulus of the folded balloon material. In FIG. 3A, a balloon cross-section is shown with the balloon inflated to pressure P31, 0.5 ATM, which for this balloon design is below its minimum first occlusion pressure. Pressure P31 is not sufficient to remove wrinkles 355 from the balloon material (doesn't overcome the flexural modulus of the balloon material). As a result, if one were to measure the apparent balloon diameter, as shown, using conventional laser measurement set-ups, then one would measure the diameter D1. In FIG. 3B, the pressure in the balloon is increased to P32, 1.0 ATM, which is a high enough pressure to effectively force the wrinkles out of the balloon material (overcome the flexural modulus of the balloon material), and the apparent balloon diameter, as shown, would measure as diameter D2, a smaller diameter than D1. In FIG. 3B, the pressure in the balloon is at or above its minimum first occlusion pressure. If many balloons of the same design are tested across a range of low pressures and random balloon folding orientations to gather pressure-diameter data pairs, then some of the data will exhibit this effect.

In preferred embodiments, the estimated minimum first occlusion pressure is increased by 0.25 ATM or less to set the value of the first occlusion pressure. This 0.25 ATM pressure increase may adjust the minimum first occlusion pressure to account for the lack of (systolic) blood pressure (120 mmHg=0.16 ATM) applied to the balloon OD in most practical test set-ups and helps assure vessel occlusion in condition one at the first occlusion pressure while limiting the amount of extra pressure that can be applied to the vessel wall to less than about 0.10 ATM (0.25 ATM−0.16 ATM=0.09 ATM), which is very safe in the short term for the most sensitive vessels, coronary arteries. In many cases, during the few seconds that it takes to stabilize the pressure in the balloon at the first occlusion pressure, a coronary artery will not be significantly stretched or damaged in the first condition. Subsequently, any vessel stretching will allow the balloon to expand (volume to increase) and thus, lower the pressure in the balloon/system, thus limiting vessel stretching. The elasticity of vessels may assure that the occlusion is not lost by the small amount of vessel stretching that may occur.

It is preferred that the nominal diameter of a compliant occlusion balloon be measured at the first occlusion pressure because this best represents the maximum vessel ID that can be occluded in the first condition.

In some embodiments, when initially inflating a non-compliant, compliant or elastic balloon using volume control, the first and second conditions are functionally irrelevant. To avoid damaging the vessel, the initial inflation volume must inflate the balloon to an OD that is below the ID (that the vessel can be forced to assume by the balloon) that can cause significant vessel damage (causes a dissection and/significant later vessel stenosis). Because of the imprecision of estimating/measuring the vessel ID, for safety reasons, the initial inflation volume must be chosen such that, effectively the balloon will not often occlude the vessel. The initial inflation volume is chosen from a chart that lists the measured vessel ID and the safe initial inflation volume or the number of volume increments required to obtain the safe initial inflation volume. With the device lever in the adjust position, the initial inflation volume may be injected into the balloon (the balloon lumen) by turning the knob, as before. In preferred embodiments of device volume control, a rotational sensor system (not shown), such as a mechanical counter, a detent clicking mechanism, or an optical angular increment counter (those with counters are preferably resettable to zero), that counts or indicates the increments of shaft 174 rotation relative to the T handle 169 may be provided. If an occlusion is not obtained, a volume increment(s) of fluid may injected into the balloon lumen from the device to inflate the balloon to a larger diameter. The volume increment(s) may be chosen such that, if the balloon was at or near the occlusion OD, the increase in balloon OD will not significantly damage the vessel (over-stretch the vessel wall). After each volume increment(s) is injected, the vessel may be tested for occlusion. This may be repeated until vessel occlusion is attained. Then latch 150 may be used as previously described to transition the balloon to perfuse or re-occlude the vessel.

According to some embodiments, it is preferred that the initial occlusion be obtained using pressure control in the first condition, and thus, compliant and non-compliant occlusion balloons are preferred over elastic balloons. These may be preferred because physicians are very familiar with adjusting the pressure of inflation-deflation devices to adjust balloon OD's (for example, angioplasty [POBA] and stent delivery systems [SDS]) and they may involve the fewest steps and least procedure time to safely attain the initial occlusion. According to some embodiments, in occlusion systems, which have a significant possibility that the vessel ID will exceed the nominal OD of the balloon chosen by the physician, compliant occlusion balloons are preferred over non-complaint balloons. In this case, compliant balloons are preferred because they do not require the balloon (the balloon catheter) to be replaced with a larger nominal OD balloon in order for the initial occlusion to be obtained and thus, provide a less expensive and a shorter procedure time.

FIG. 4 is a flow diagram of process 400 to inflate a balloon to occlude a blood vessel, to perfuse the vessel, and to treat an occluded region. Process 400 may be a process to inflate, a deflated balloon having folds and coupled to an inflation-deflation device (e.g., device 100 or 200) as described herein. Descriptions above the folded balloon of FIG. 3 may apply here as well. Process 400 may be a process that includes occluding and perfusing a blood vessel using a balloon or occlusion device coupled to an inflation-deflation device (e.g., device 100 or 200) as described herein.

At Block 402 the balloon inflation/deflation system is aspirated, including a mechanical pressure gauge. The mechanical pressure gauge may be attached or in fluid communication with a syringe of an inflation-deflation device (e.g., device 100 or 200) as described herein. Such aspirating may include descriptions above for aspirating device 100 or 200. The gauge may be aspirated by removing any gas or air from within the gauge and replacing it with fluid.

Angioplasty balloon inflation/deflation systems are routinely aspirated to assure that the indeflator can provide enough volume change and is easy (takes less time) to inflate the balloon to the desired (high) pressure. However, the complete aspiration of the mechanical pressure gauge is generally overlooked because you have to orient the mechanical pressure gauge in a special way to get all the air out of it. The hole in mechanical pressure gauge that is in communication with the balloon inflation fluid must be pointed up to remove all the air from the gauge during aspiration procedures. This means that the physician must hold the indeflator with the gauge's scale under the indeflator, where it can't be seen, during aspiration. This is not the usual indeflator holding position. Mechanical pressure gauges are usually less expensive and more reliable than electronic pressure gauges in this application. In some compliant balloon catheter-ICVI systems, it can be undesirable to forget/not know how to aspirate the mechanical pressure gauge because the higher system compliance may cause the OD of the balloon to creep (get larger) during occlusion and stretch the vessel wall to an undesirable degree. The greater the stretch of the vessel a the greater the chance of a stenotic reaction at the stretch site.

Block 402 may also include positioning the catheter in the vessel, such as at a target location to perform occlusion; and at which or from which to provide treatment.

At Block 404 the balloon is inflated to a first occlusion pressure using the ICVI. The first occlusion pressure of the balloon may be predetermined or selected (e.g., such as noted for FIG. 5). Block 404 may include descriptions herein for inflating to a first occlusion pressure. For instance, at this pressure, the balloon may be in perimeter contact with the vessel; and have a fold or folds and an irregular shape. In this case, the first occlusion pressure in the balloon may be the pressure required to inflate the balloon into contact with the vessel wall (overcome blood pressure) plus the pressure required to press any folds in the balloon together (e.g., effectively force the wrinkles out of the balloon material) or cause the balloon to conform to the vessel wall to prevent a leakage path through the balloon fold(s) or bends in the vessel wall (overcome balloon flexural modulus). Also, block 404 may include place the inflation device lever into the adjust position and to turn the knob of the device (adjusts the syringe/proximal system volume) at a rate required to create/observe a pressure of about 1 ATM on the gauge and to continue turning until the rate of turning required decreases noticeably and then to turn the knob, as required, to adjust the pressure reading to a specified first occlusion pressure for a short time until the pressure reading stabilizes.

At Block 406 the vessel is tested for vessel occlusion. Block 406 may include descriptions herein for testing for an occlusion. In some cases, testing for an occlusion includes injecting contrast down another lumen of the catheter or down another catheter (such as a guide catheter) and observing the wash out, if any, of the contrast under fluoroscopy.

At Block 408, the results of the test for vessel occlusion are determined. If the vessel is not occluded, the process continues to Block 410. If it is occluded, the process continues to Block 412.

At Block 410 the balloon pressure is increased by (e.g., the balloon is inflated with) one pressure increment using the ICVI. Block 410 may include descriptions herein for inflating with one pressure increment. This may be only one single increment of pressure. The increment of pressure of the balloon may be predetermined or selected, such as noted herein. Block 410 may include inflating the balloon with equal increments of fluid pressure, such as by using an inflation deflation device described herein, until a blood vessel of a person with a beating heart is occluded (e at block 408). In some cases, Block 410 may be increasing the balloon with an increment of volume (instead of pressure) as described herein for volume control.

Block 410 may include inflating a balloon already inflated to a nominal pressure, to an occlusion pressure by rotating knob 130 when the switch is in the adjust position. Once occlusion is reached, the switch may be moved to an adjacent position, the lock position, to lock the device (e.g., and system) at the occlusion pressure, without transitioning to the release position (and releasing the occlusion pressure).

Once in the lock position, occlusion pressure may be maintained during treatment of a target region, such as by infusion of a treatment agent or drug.

At Block 412 the volume of the balloon inflation system (e.g., excluding the ICVI) is increased using the ICVI to deflate balloon and perfuse the vessel. Block 412 may include descriptions herein for deflating with one volume increment to perfuse a vessel. Block 412 may include decreasing the volume of fluid in the balloon (e.g., the balloon is deflated) by one volume increment using the ICVI. This may be only one single increment of volume. The increment of volume of the balloon may be predetermined or selected, such as noted herein.

Block 412 may include using latch 150 to remove a predetermined volume of fluid from the balloon sufficient to allow profusion of the blood vessel by blood pressure of a person, having a beating heart. Block 412 may include deflating the balloon by moving the switch from the adjust to the adjacent lock position, and then transitioning latch 150 to the perfuse position.

At Block 414 the occlusion volume of the balloon inflation system is returned to using the ICVI, to re-inflate balloon and occlude the vessel. Block 414 may include descriptions herein for re-inflating with one volume inclement to occlude a vessel. Block 414 may include increasing the volume of the balloon (or balloon inflation system) by the volume removed at block 412, such as to re-occlude the vessel. This may be only one single increment of volume.

Block 414 may include re-inflating the balloon to the same safe occlusive OD, by transitioning latch 150 from the perfuse, to the occlude position, while the switch is in the lock position. Re-inflating may include a single movement of a plunger (e.g., plunger 210) to push the volume of fluid to cause the balloon to re-occlude the blood vessel.

At Block 416 a region of the occluded vessel may be treated. Block 416 may include descriptions herein for treating an occluded vessel. At block 416, a treatment agent or drug may be used to treat the occluded region (e.g., a treatment or target region). The occlusion balloon may then be positioned proximal, near, and/or distal to the target region. In some embodiments such a treatment may include infusing a drug or progenitor cells into a portion of the vessel re-occluded at block 414 such that the injection treats the vessel and is not pumped away by the heart, until profusion at block 418.

At Block 418 the volume of the balloon inflation system (e.g., excluding the ICVI) is increased using the ICVI to deflate balloon and perfuse the vessel. Block 418 may include descriptions for Block 412.

At Block 420, it is determined whether the treatment is complete. If the treatment is not complete, the process returns to Block 414. Blocks 414-420 may be repeated, to repeat a treatment procedure at block 416. Moreover, transition from block 414 to 418 may include performing block 418 prior to a threshold period of time after occlusion at block 414.

If the treatment is complete, the process continues to Block 422 and ends. The process may be terminated by deflating the balloon by moving the switch from the adjust position to the, optionally adjacent, release position; by reverse rotating knob 130; or by transitioning latch 150 to the perfuse position. Block 422 may include removing the catheter from the vessel.

Using process 400 (and the systems 100 or 200) a vessel may be occluded multiple times during multiple treatments of the same target region, between which the vessel may be perfused to avoid ischemia and other damage to the treatment region during treatment (e.g., such as noted herein).

Such occlusion and perfusion may be accomplished by transitioning latch 150 from the occlude position, to the perfuse position to remove a volume of fluid from the system (e.g., block 412), and back to the occlude position to replace the volume of fluid into the system (e.g., block 414). The volume may be predetermined and removed regardless of or without concern for the amount of pressure removed and replaced. One advantage of removing a predetermined volume of fluid from the system to perfuse the blood vessel is that the same volume can be pushed back into the balloon to re-occlude the vessel. Moreover, the volume can be removed with a single transition of the latch to the perfuse position (or movement of a single plunger to location LL2) and pushed back with a single transition of the latch to the occlude position (or movement of a single plunger back to location LL1).

The repeated re-inflation of the balloon to the same safe occlusive OD may be accomplished by returning the syringe volume to the same volume it was adjusted to when the safe occlusive OD was originally attained (e.g., by transitioning latch 150 between the perfuse to the occlude position, while the switch is in the lock position). The re-inflation to the safe occlusive OD/deflation cycle may be performed at least three (3) times during a therapy (e.g., by transitioning latch 150 between the perfuse and the occlude position, while the switch is in the lock position). In some embodiments, the balloon is at a single location within the blood vessel during process 400.

FIG. 5 is a flow diagram of process 500 to estimate a first occlusion pressure of a type of balloon. Process 500 may include using or extrapolating from measured test pressures and outer diameters; and may use a balloon coupled to an inflation-deflation device (e.g., device 100 or 200) as described herein. For instance, the first occlusion pressure of a balloon may be determined from testing using a test set-up to simulate the vessel(s) or may be calculated by a procedure that involves measuring the OD of the balloon at increasing pressures in a bath at body temperature. Process 500 may be applied to balloons that include folds or wrinkles. Descriptions above the folded balloon of FIG. 3 may apply here as well.

At Block 502 an occlusion catheter is selected for testing. The catheter is a balloon catheter with a balloon for occluding a living human patient's blood vessel. The balloon may be a folded balloon as noted herein. In some cases, a "folded" balloon has multiple folds (e.g., when completely or substantially deflated). Such a balloon may have 2, 3, 4, 5, 6 or 8 folds. The balloon may have substantial uninflated folds or wrinkles when inflated below or at a first occlusion pressure, wherein the balloon has a substantially circular cross-section above the first occlusion.

It is usually only necessary to test each balloon's design and processing limits, such as for certain designed type and size of balloon. The minimum first occlusion pressure of a balloon design may be the pressure at which the balloon attains a substantially circular cross-section, within a predetermined limit (e.g., a difference in balloon diameter of less than or equal to 0.1 mm, for a coronary occlusion balloon).

At Block 504 the balloon is inflated to about ½ its nominal volume. At Block 504 the occlusion balloon may be inflated from being deflated (e.g., having no fluid or gas within the balloon). To inflate the balloon at block 504, or other blocks of FIG. 5, the occlusion balloon may be inflated using device 100 or 200 as described herein, such as by rotating knob 130 when the switch is in the adjust position.

At Block 506 the balloon is inflated to a low beginning pressure, say 0.1 ATM.

At Block 508 the balloon OD is measured, and the pressure (x) and OD (y) data pair are recorded.

At Block 510 it is determined if the highest test pressure has been reached? If not at Block 512, the balloon pressure is increased to the next higher test pressure. If so, at Block 514 it is determined if the last catheter balloon been tested. Block 514 may be determined by selecting an error threshold for the test/results, such as based on a statistical analysis using the number of catheters tested.

At Block 516 the (x,y) data pairs are plotted and the estimated minimum occlusion pressure is determined (e.g., estimated or calculated). Thus, the minimum first occlusion pressure may be estimate by partially inflating the balloon to ½ it's inflated by volume, and then adding small inflation pressure steps applied at the lower test pressures. The minimum first occlusion pressure may be estimated as the largest ending pressure at which some of the measured maximum outer diameters decrease or stay equal when their pressure is increased. At this point, any folds may have been forced out of the balloon. Determining or detecting whether a balloon has substantial uninflated folds or wrinkles; or has a substantially circular cross-section, may be performed by viewing the inflated balloon, with or without the aid of an optical magnifier, such as a microscope or magnifying glass. The outer diameter to inflation pressure curve may be inconsistent due to uninflated folds in the balloon.

Another way to estimate the minimum first occlusion pressure is to plot the pressure (x)-diameter (y)-data pairs of this data and perform a standard linear regression analysis. At the higher pressures, the data points will cluster near a straight line (the linear regression line). However, when you examine the curve at the lower pressures, the data points will begin to distribute themselves much further away from this straight line. The pressure at which the data points begin to distribute themselves further away from this straight line is the estimated minimum first occlusion pressure.

At Block 518 0.25 ATM (systolic adjustment) is added to the estimated minimum occlusion pressure to obtain the first occlusion pressure. This 0.25 ATM pressure increase may adjust the minimum first occlusion pressure to account for the lack of (systolic) blood pressure (120 mmHg=0.16 ATM) applied to the balloon OD in most practical test set-ups.

In the foregoing specification, specific embodiments are described. For example, devices, structures, inflation-deflation devices, extension tubes, stopcocks, catheters, cannulas, balloons, occlusion devices, and processes described herein may be used to treat blood vessels of a human being, such as veins or arteries, including those of the human heart. However, various modifications and changes may be made thereto without departing from the broader spirit and scope of embodiments as set forth in the claims. The specification and drawings are, accordingly, to be regarded in an illustrative rather than a restrictive sense.

What is claimed is:

1. Apparatus comprising:
   a releasable latch positioning a proximal housing relative to a distal housing, the distal housing coupled to a syringe barrel and a rotational knob coupled to the distal housing;
   at least one plunger disposed within the syringe barrel, wherein the rotational knob is coupled to the plunger by a screw mechanism to move the plunger along a length of the syringe barrel when the rotational knob is rotated, the screw mechanism having a rotational lock to prevent the plunger from moving when in a locked position;

wherein the latch defines an occlusion position to releasably lock the plunger at a first location along the length of the syringe and a perfusion position to releasably lock the plunger at a second location along the length proximal to the occlusion location; and a three-position switch coupled to the screw mechanism, the switch comprising a release position, an adjust position that allows the rotational knob to rotate, and a lock position, wherein the lock position is adjacent to the adjust position.

2. The apparatus of claim 1 wherein the rotational knob is a first knob and the latch comprises a second knob that when pulled away from the distal housing puts the latch in the perfusion position and that when pushed towards the distal housing puts the latch in the occlusion position, wherein when in the perfusion position, the lock is able to resist at least 1.5 ATM of back pressure, and wherein when in the occlusion position, the lock is able to resist at least 6 ATM of back pressure.

3. The apparatus of claim 2 wherein when the plunger is located along the length of the syringe barrel, the occlusion position and the perfusion position define two position locations within the syringe to repeatedly cause: 1) a volume of fluid to be drawn into the syringe when the latch is pulled into the perfusion position, and 2) then the volume of fluid to be pushed out of the syringe when the latch is returned to the occlusion position.

4. The apparatus of claim 2 wherein the screw mechanism includes a plurality of incremental pressure or volume positions that locate the plunger at a plurality of locations along the length of the syringe that cause incremental and equal increases or decreases in pressure or volume output by the syringe when the syringe is filled with fluid and the plunger is transition between the positions.

5. The apparatus of claim 1 wherein when in the adjust position, the lock allows the plunger to move to a plurality of positions in response to a rotational force applied to the knob, but prevents the plunger from moving in response to the back pressure applied to a head of the plunger.

6. An apparatus comprising:
a distal housing coupled to a syringe barrel;
a rotational knob coupled to the distal housing;
a screw mechanism coupling the rotational knob to a plunger within the syringe barrel to move the plunger along a length of the syringe barrel, the screw mechanism having a rotational lock to prevent the plunger from moving when in a locked position;
a three-position switch coupled to the screw mechanism, the switch comprising a release position, an adjust position that allows the rotational knob to rotate, and a lock position, wherein the lock position is adjacent to the adjust position.

7. The apparatus of claim 6 wherein when in the locked position, the switch prevents the knob from rotating.

8. The apparatus of claim 7 wherein when in the locked position, the lock prevents the plunger from moving in response to at least 6 ATM of back pressure applied to a head of the plunger, and prevents the knob from rotating in response to a rotational force applied to the knob or in response to the back pressure applied to a head of the plunger;

wherein when in the release position, the lock allows the plunger to move in response to a back pressure applied to the plunger head or a rotational force applied to the knob; and wherein when in the adjust position, the lock allows the plunger to move to a plurality of positions in response to a rotational force applied to the knob, but prevents the plunger from moving in response to the back pressure applied to a head of the plunger.

9. The apparatus of claim 8 wherein when in the adjust position the plunger may be moved to a plurality of incremental position locations along a length of the syringe barrel in response to a rotational force applied to the knob, the positions causing equal changes in pressure or volume to be output by the syringe when the syringe is filled with a liquid.

10. The apparatus of claim 6 wherein the switch can be transitioned between the adjust position and the locked position without entering the release position.

11. The apparatus of claim 6 wherein the switch comprises a single switch having the adjust position located between the release position and the locked position, or the locked position located between the release position and the adjust position.

12. The apparatus of claim 6 wherein when in the adjust position, the lock allows the plunger to move to a plurality of positions in response to a rotational force applied to the knob, but prevents the plunger from moving in response to the back pressure applied to a head of the plunger.

13. An apparatus comprising:
a releasable latch positioning a proximal housing relative to a distal housing, the distal housing coupled to a first syringe barrel;
a first plunger within the first syringe barrel, the first plunger coupled to a first shaft defining a second syringe barrel within the first shaft;
a screw mechanism coupling the second syringe barrel and the first plunger to a rotating knob of the proximal housing to move the first plunger along a length of the first syringe barrel when the knob is rotated;
the releasable latch coupling the proximal housing to the second plunger, and to repeatedly position the second plunger within the second syringe barrel to repeatedly:
1) releasably lock the second plunger at a first location along a length of the second syringe barrel, and 2) to releasably lock the second plunger at a second location along a length of the second syringe barrel.

14. The apparatus of claim 13 wherein the screw mechanism moves the first plunger to locations within the first syringe barrel that provide equal pressures or volume increases in the first syringe barrel.

15. The apparatus of claim 13 wherein the first plunger and the screw mechanism are configured to increase a pressure or volume of fluid in the syringe to a pressure or volume to cause a balloon to occlude a flow of blood in a human blood vessel, and wherein the second plunger and the releasable latch are configured to repeatedly translate the second plunger between the first latched position to cause perfusion and the second latched position to cause re-occlusion of the blood vessel.

16. An apparatus comprising:
a releasable latch positioning a proximal housing relative to a distal housing, the distal housing coupled to a syringe barrel and a rotational knob coupled to the distal housing; and
at least one plunger disposed within the syringe barrel, wherein the rotational knob is coupled to the plunger by a screw mechanism to move the plunger along a length of the syringe barrel when the rotational knob is rotated, the screw mechanism having a rotational lock to prevent the plunger from moving when in a locked position;

wherein the latch defines an occlusion position to releasably lock the plunger at a first location along the length of the syringe and a perfusion position to releasably lock the plunger at a second location along the length proximal to the occlusion location; and wherein when in the perfusion position, the lock is able to resist at least 1.5 ATM of back pressure, and wherein when in the occlusion position, the lock is able to resist at least 6 ATM of back pressure.

17. The apparatus of claim 16 further comprising a three-position switch coupled to the screw mechanism, the switch comprising a release position, an adjust position, and a lock position, wherein the lock position is adjacent to the adjust position, wherein when in the locked position, the switch prevents the knob from rotating.

18. An apparatus comprising:
a releasable latch positioning a proximal housing relative to a distal housing, the distal housing coupled to a syringe barrel and a rotational knob coupled to the distal housing; and at least one plunger disposed within the syringe barrel, wherein the rotational knob is coupled to the plunger by a screw mechanism to move the plunger along a length of the syringe barrel when the rotational knob is rotated, the screw mechanism having a rotational lock to prevent the plunger from moving when in a locked position;

wherein the latch defines an occlusion position to releasably lock the plunger at a first location along the length of the syringe and a perfusion position to releasably lock the plunger at a second location along the length proximal to the occlusion location; and wherein the rotational knob is a first knob and the latch comprises a second knob that when pulled away from the distal housing puts the latch in the perfusion position and that when pushed towards the distal housing puts the latch in the occlusion position.

19. The apparatus of claim 18 further comprising a three-position switch coupled to the screw mechanism, the switch comprising a release position, an adjust position, and a lock position, wherein the lock position is adjacent to the adjust position, wherein when in the locked position, the switch prevents the knob from rotating.

20. An apparatus comprising:
a distal housing coupled to a syringe barrel;
a rotational knob coupled to the distal housing; and
a screw mechanism coupling the rotational knob to a plunger within the syringe barrel to move the plunger along a length of the syringe barrel;
wherein when in the locked position, the lock prevents the plunger from moving in response to at least 6 ATM of back pressure applied to a head of the plunger, and prevents the knob from rotating in response to a rotational force applied to the knob or in response to the back pressure applied to a head of the plunger.

21. The apparatus of claim 20 further comprising a three-position switch coupled to the screw mechanism, the switch comprising a release position, an adjust position, and a lock position, wherein the lock position is adjacent to the adjust position, wherein when in the locked position, the switch prevents the knob from rotating.

22. An apparatus comprising:
a distal housing coupled to a syringe barrel;
a rotational knob coupled to the distal housing; and
a screw mechanism coupling the rotational knob to a plunger within the syringe barrel to move the plunger along a length of the syringe barrel;
wherein when in the release position, the lock allows the plunger to move in response to a back pressure applied to the plunger head or a rotational force applied to the knob; and wherein when in the adjust position, the lock allows the plunger to move to a plurality of positions in response to a rotational force applied to the knob, but prevents the plunger from moving in response to the back pressure applied to a head of the plunger.

23. The apparatus of claim 22 further comprising a three-position switch coupled to the screw mechanism, the switch comprising a release position, an adjust position, and a lock position, wherein the lock position is adjacent to the adjust position, wherein when in the locked position, the switch prevents the knob from rotating.

* * * * *